(12) United States Patent
Jawrani et al.

(10) Patent No.: US 11,547,579 B2
(45) Date of Patent: Jan. 10, 2023

(54) SYSTEMS AND METHODS FOR SIZING AND INTRODUCTION OF SOFT-TISSUE ALLOGRAFTS

(71) Applicant: Arthrosurface, Inc., Franklin, MA (US)

(72) Inventors: Nikhil T. Jawrani, Framingham, MA (US); Steven W. Ek, Bolton, MA (US)

(73) Assignee: Arthrosurface, Inc., Franklin, MA (US)

( * ) Notice: Subject to any disclaimer, the term of this patent is extended or adjusted under 35 U.S.C. 154(b) by 231 days.

(21) Appl. No.: 16/449,022

(22) Filed: Jun. 21, 2019

(65) Prior Publication Data

US 2019/0388246 A1 Dec. 26, 2019

Related U.S. Application Data

(60) Provisional application No. 62/687,901, filed on Jun. 21, 2018.

(51) Int. Cl.
| | |
|---|---|
| *A61B 17/58* | (2006.01) |
| *A61B 17/60* | (2006.01) |
| *A61F 2/00* | (2006.01) |
| *A61F 2/46* | (2006.01) |
| *A61L 27/36* | (2006.01) |
| *A61F 2/30* | (2006.01) |
| *A61B 17/04* | (2006.01) |
| *A61F 2/42* | (2006.01) |

(52) U.S. Cl.
CPC .......... *A61F 2/4657* (2013.01); *A61L 27/362* (2013.01); *A61L 27/365* (2013.01); *A61B 17/0482* (2013.01); *A61F 2002/3008* (2013.01); *A61F 2002/30754* (2013.01); *A61F 2002/4258* (2013.01); *A61F 2002/4615* (2013.01); *A61F 2002/4658* (2013.01)

(58) Field of Classification Search
USPC ....................................... 606/95, 99
See application file for complete search history.

(56) References Cited

U.S. PATENT DOCUMENTS

| | | |
|---|---|---|
| 3,745,590 A | 7/1973 | Stubstad |
| 4,450,591 A | 5/1984 | Rappaport |
| 5,507,822 A | 4/1996 | Bouchon et al. |
| 5,645,605 A | 7/1997 | Klawitter |
| 6,017,366 A | 1/2000 | Berman |
| 6,168,631 B1 | 1/2001 | Maxwell et al. |
| 8,092,547 B2 | 1/2012 | Lepow et al. |

(Continued)

FOREIGN PATENT DOCUMENTS

FR 2763835 12/1998

OTHER PUBLICATIONS

Kokkalis, Zinon T. and Robert W. Weiser. "Trapezium Resection With Suspension and Interposition Arthroplasty Using Acellular Dermal Allograft for Thumb Carpometacarpal Arthritis" *The Journal Of Hand Surgery* 2009, 34A, 1029-1036.

(Continued)

*Primary Examiner* — Sameh R Boles
(74) *Attorney, Agent, or Firm* — Goodwin Procter LLP

(57) ABSTRACT

The present disclosure includes systems, methods, kits, and individual tools (e.g., trial sizers and delivery devices) for medical procedures involving a soft-tissue allograft for the correction of skeletal impairments (e.g., misalignments, arthritis, etc.).

11 Claims, 32 Drawing Sheets

(56) References Cited

U.S. PATENT DOCUMENTS

| | | |
|---|---|---|
| 8,167,953 B2 | 5/2012 | Warburton |
| 8,641,770 B2 | 2/2014 | Scheker |
| 8,834,568 B2 | 9/2014 | Shapiro |
| 9,119,613 B2 | 9/2015 | Gannoe et al. |
| 9,364,328 B2 | 6/2016 | Southard et al. |
| 9,538,996 B2 | 1/2017 | Patel et al. |
| 2001/0012942 A1* | 8/2001 | Estes .............. A61F 2/4611 606/105 |
| 2004/0049270 A1 | 3/2004 | Gewirtz |
| 2005/0152881 A1 | 7/2005 | Mills et al. |
| 2006/0178748 A1 | 8/2006 | Dinger et al. |
| 2006/0241777 A1 | 10/2006 | Partin et al. |
| 2006/0251629 A1 | 11/2006 | Mills et al. |
| 2007/0021839 A1 | 1/2007 | Lowe |
| 2007/0031508 A1 | 2/2007 | Armstrong et al. |
| 2007/0233272 A1 | 10/2007 | Boyce et al. |
| 2008/0004657 A1 | 1/2008 | Obermiller et al. |
| 2009/0061389 A1 | 3/2009 | Lomicka et al. |
| 2010/0016967 A1 | 1/2010 | Weiss et al. |
| 2010/0256758 A1 | 10/2010 | Gordon et al. |
| 2011/0054627 A1 | 3/2011 | Bear |
| 2011/0295379 A1 | 12/2011 | Shohat |
| 2012/0158153 A1 | 6/2012 | Hardenbrook et al. |
| 2013/0282121 A1 | 10/2013 | Prewett |
| 2014/0074247 A1 | 3/2014 | Ohashi et al. |
| 2017/0189197 A1 | 7/2017 | Werber et al. |
| 2017/0348088 A1 | 12/2017 | Bunce et al. |

OTHER PUBLICATIONS

Vitale et al., "Trapezium Prosthetic Arthroplasty (Silicone, Artelon, Metal, and Pyrocarbon)" *Hand Clin.* 2013, 29, 37-55.

Wise, David Miller. "New technique: AlloDerm® interposition arthroplasty of thumb carpo-metacarpal joint" *Journal of Biomedical Engineering and Informatics* 2016, 2(2), 36-46.

Yao et al., "Preserving the Posttrapeziectomy Space with a Human Acellular Dermal Matrix Spacer: A Pilot Case Series of Patients with Thumb Carpometacarpal Joint Arthritis" *PRS GO* 2013, 7 pages.

* cited by examiner

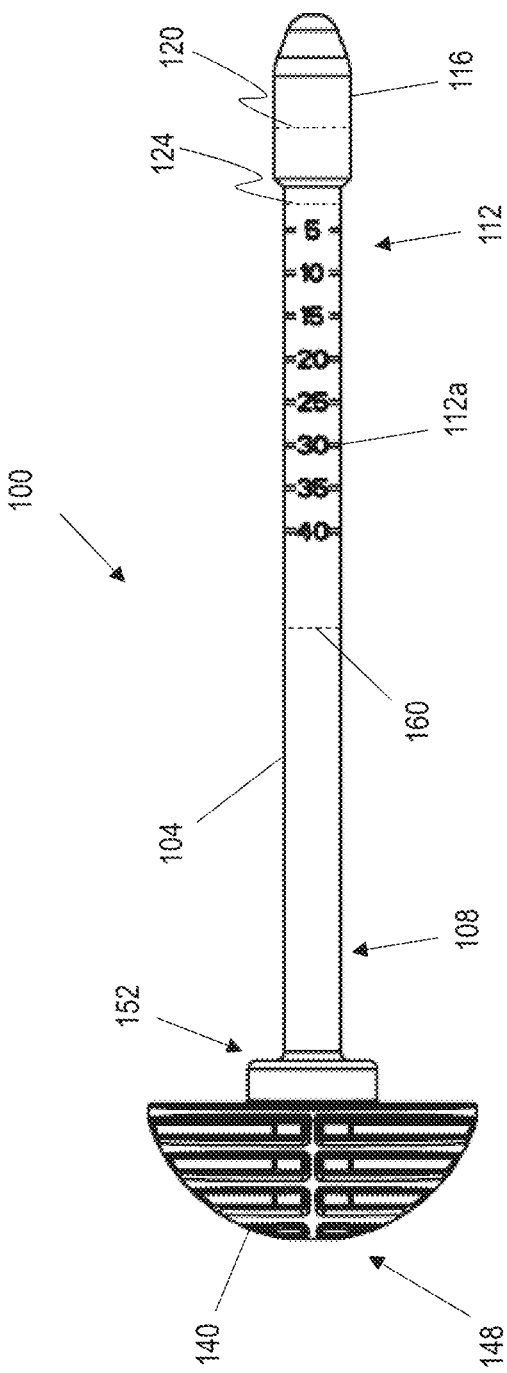

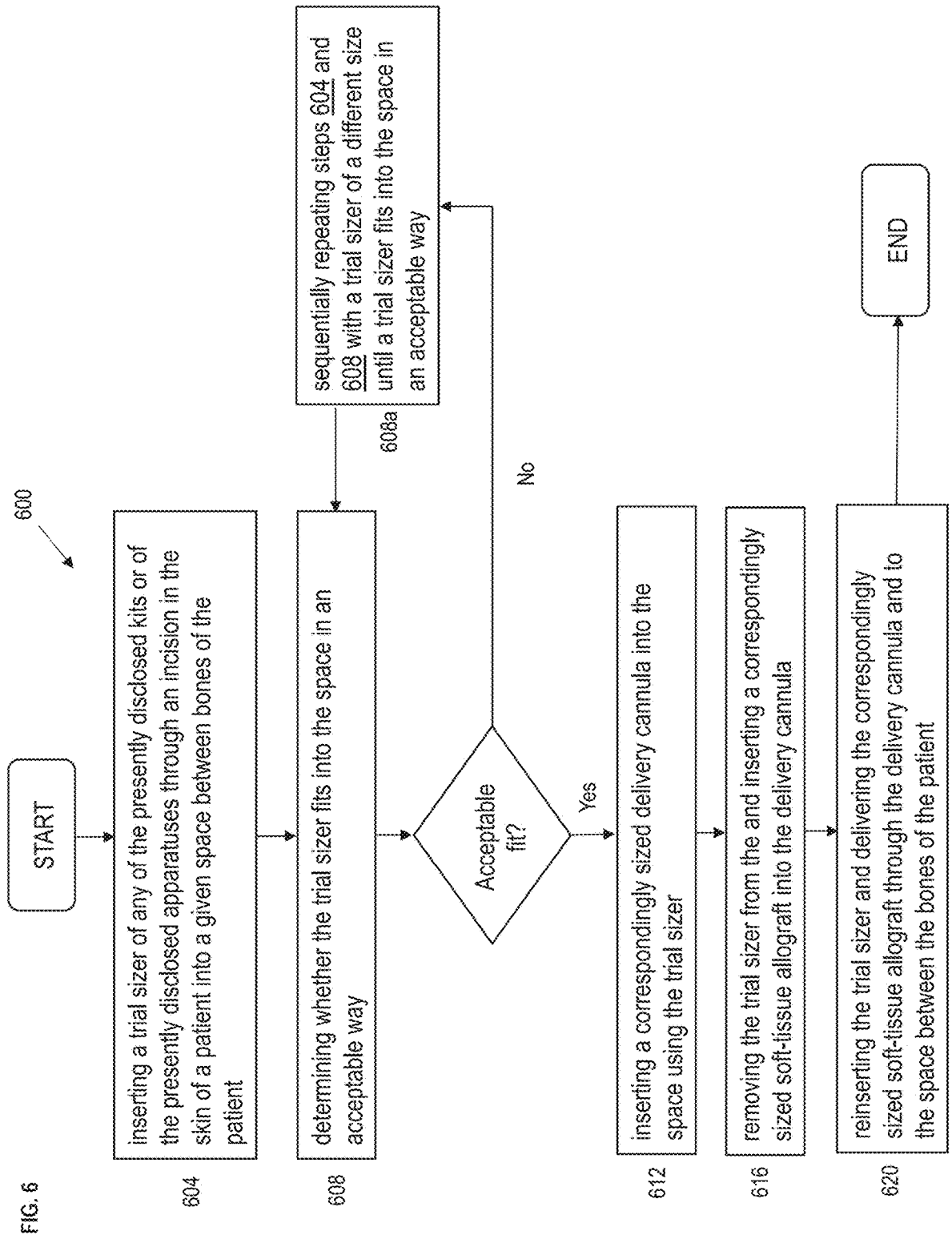

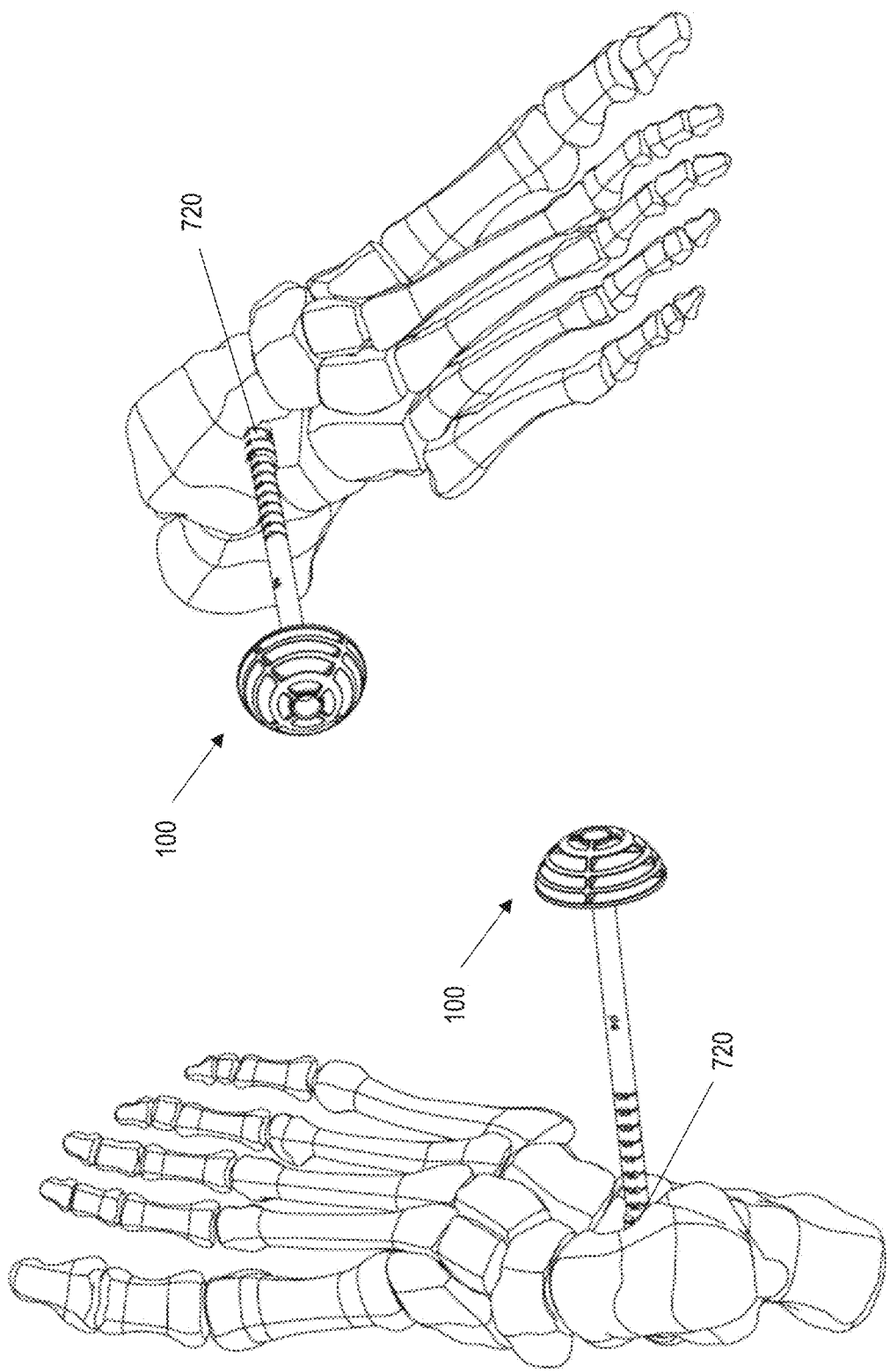

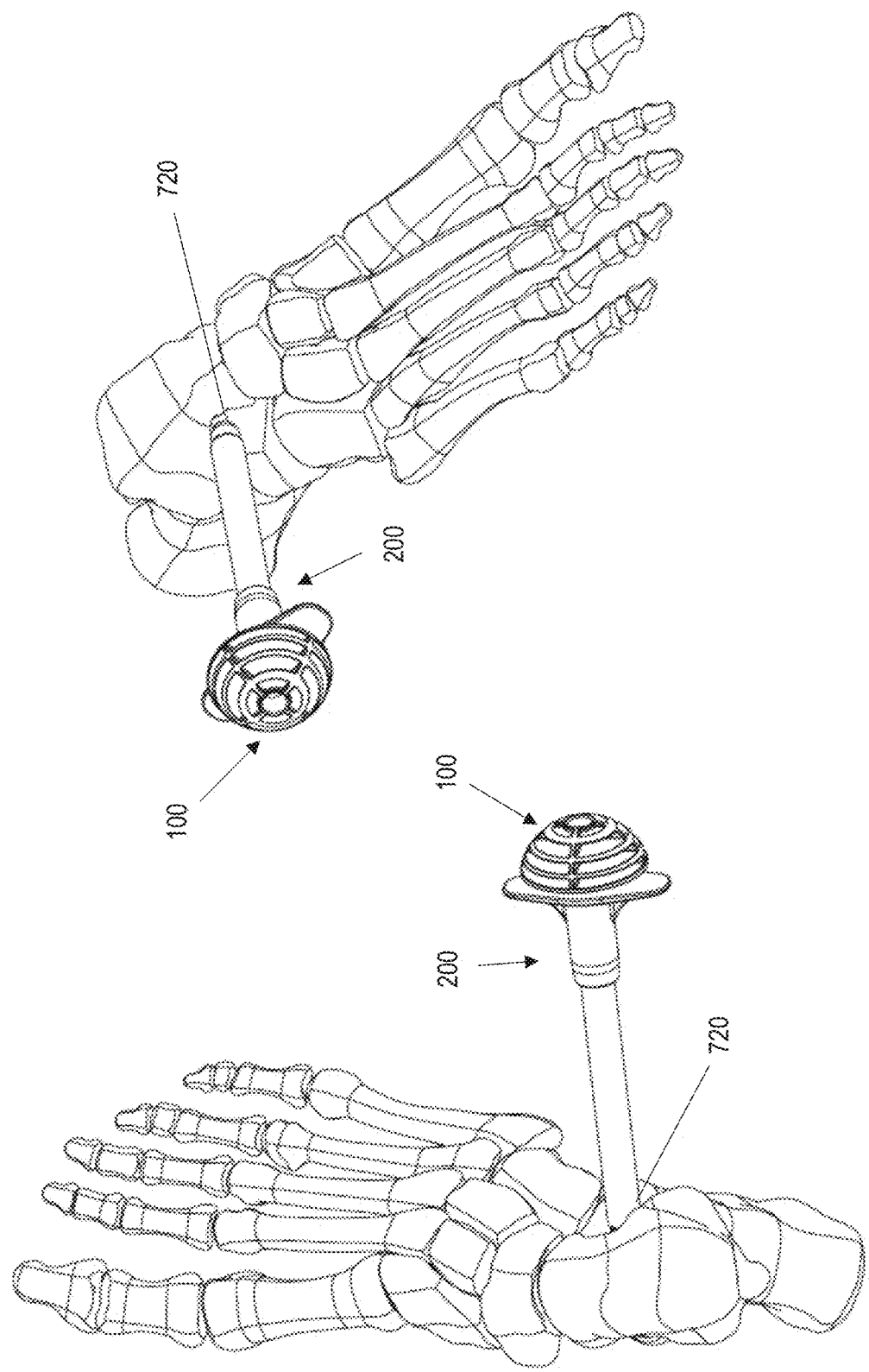

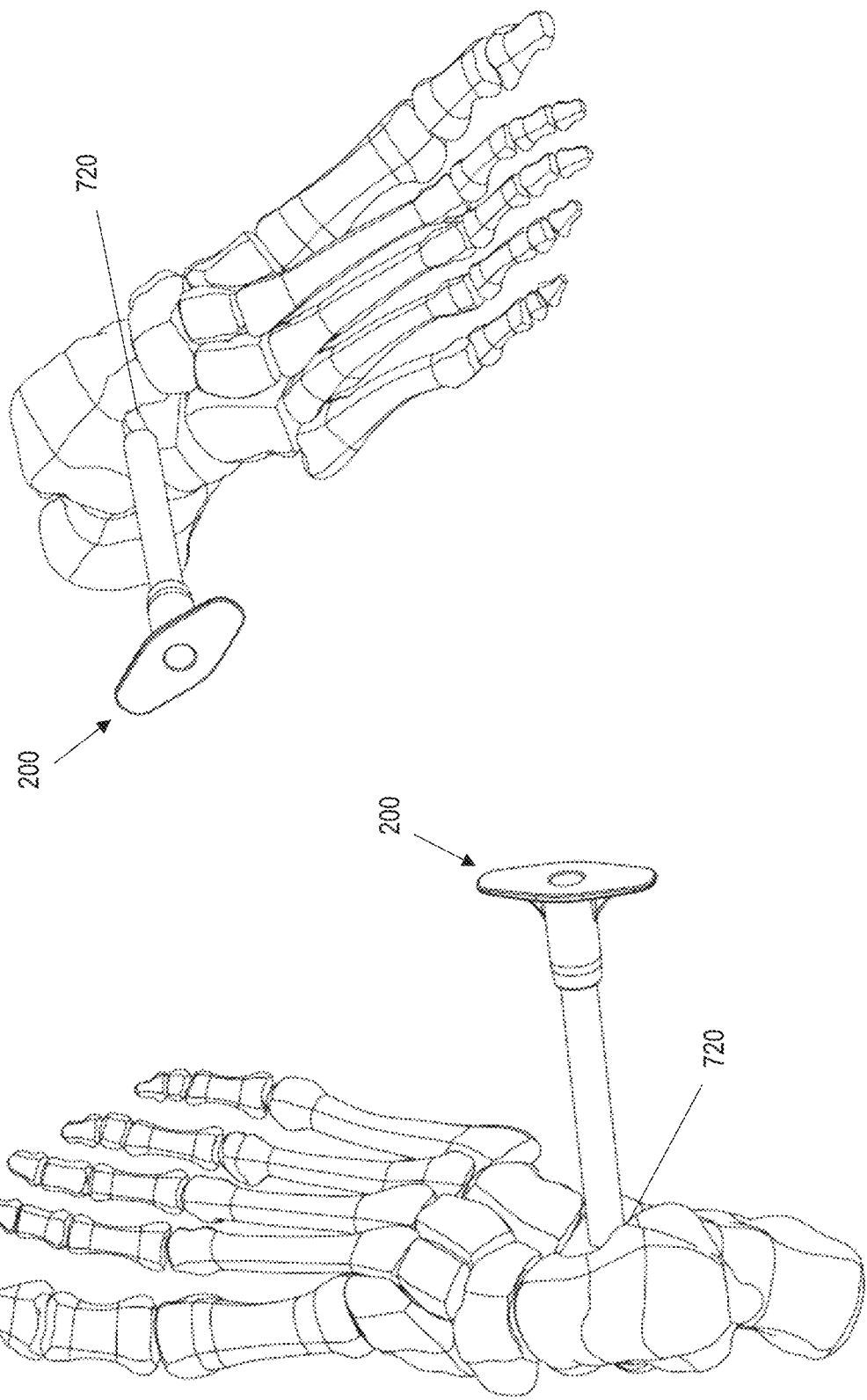

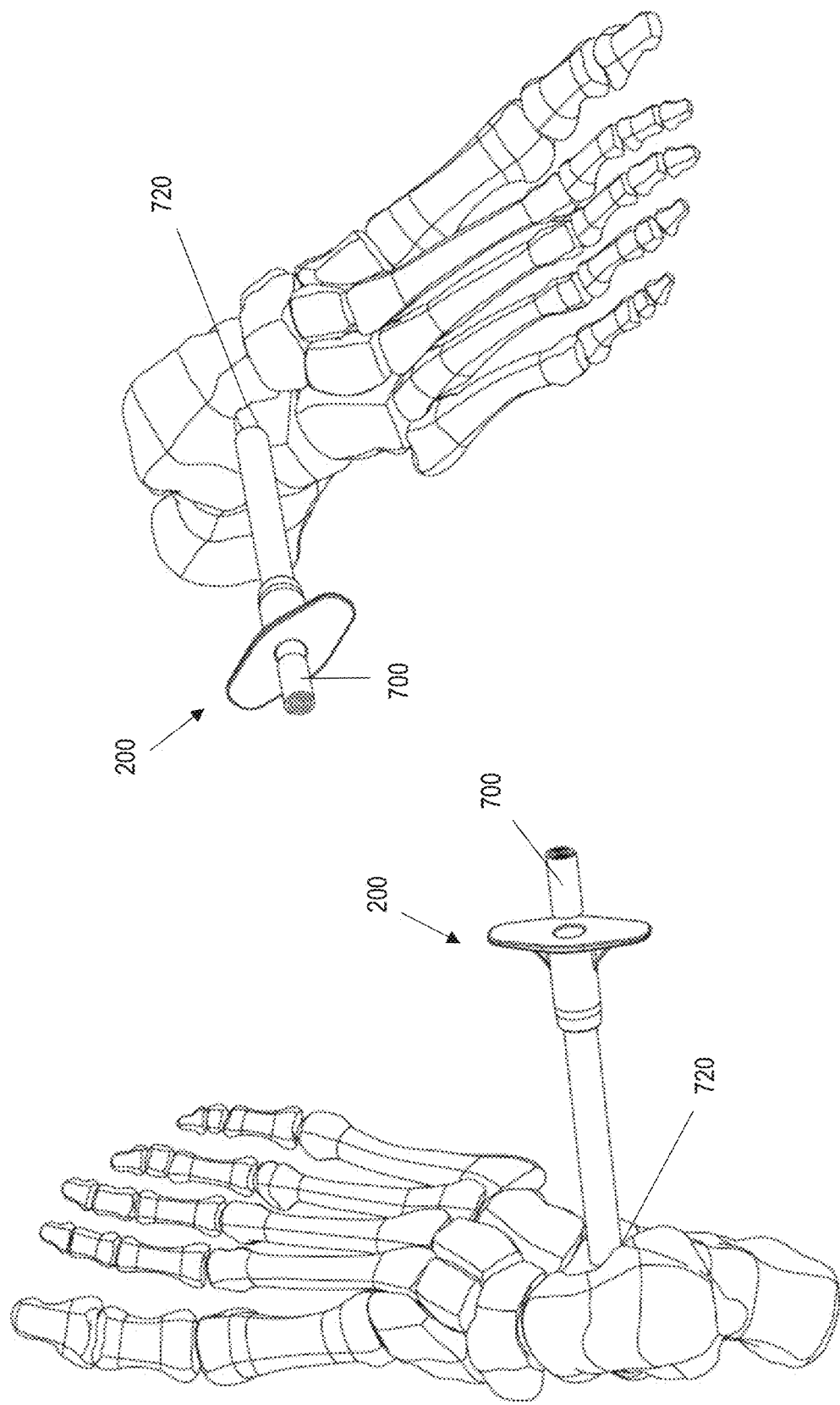

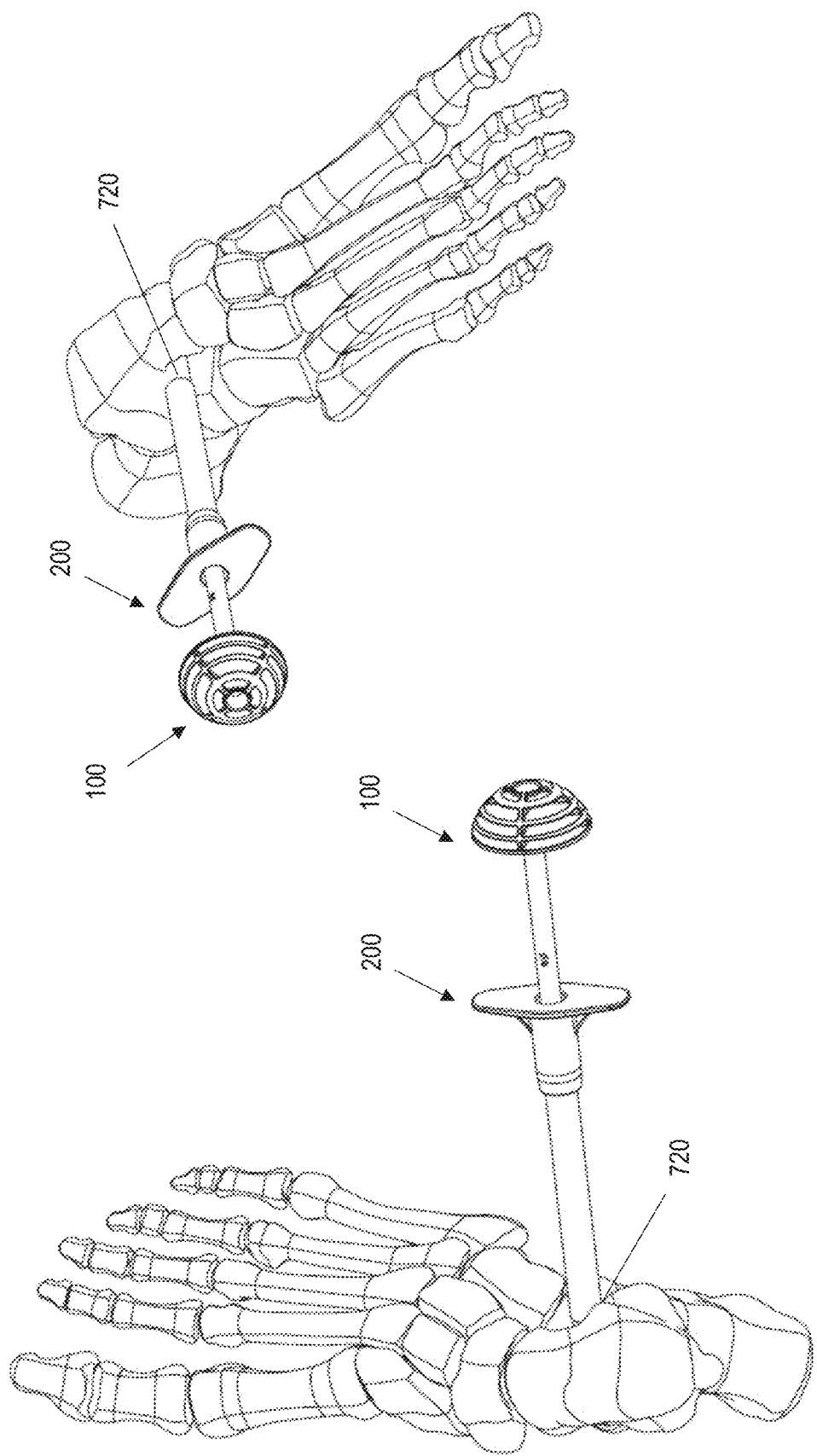

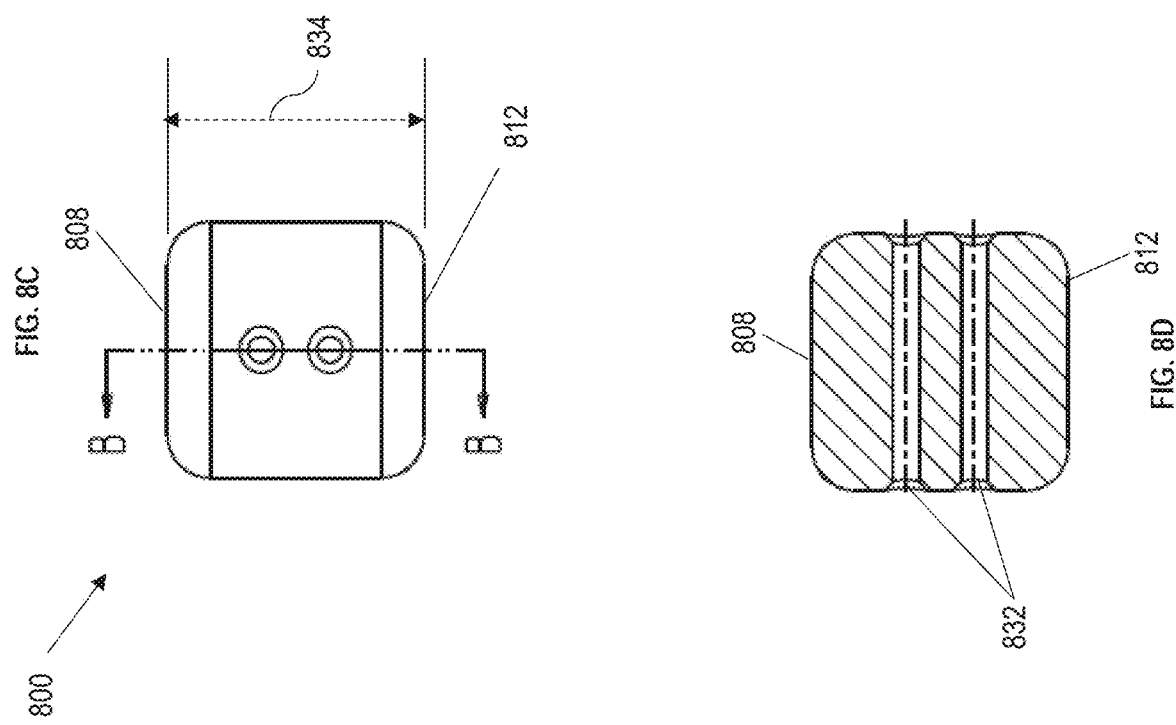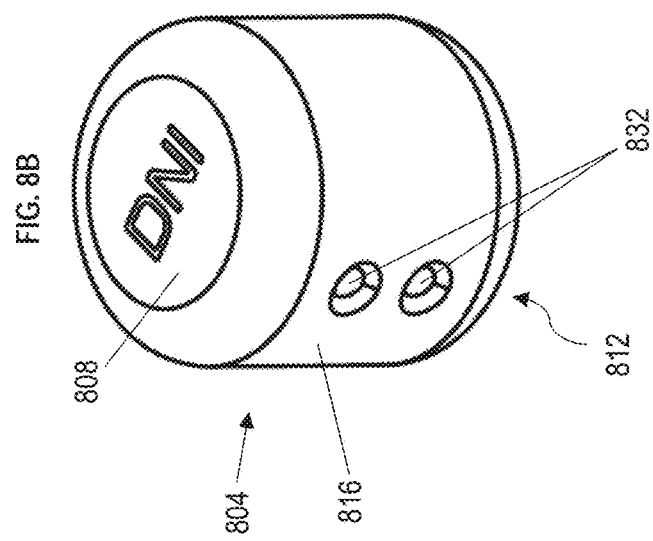

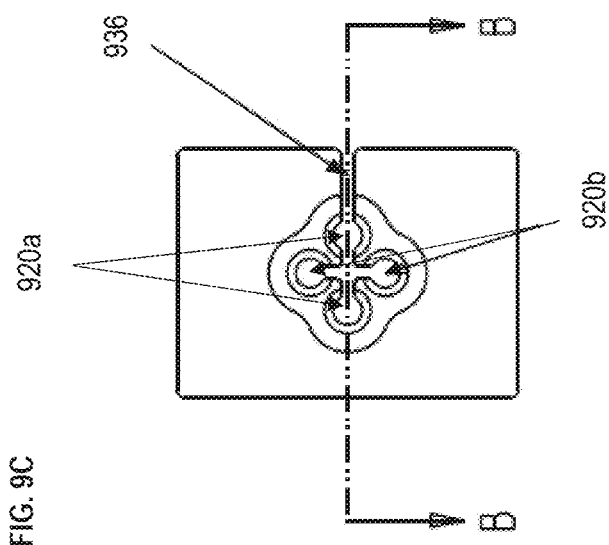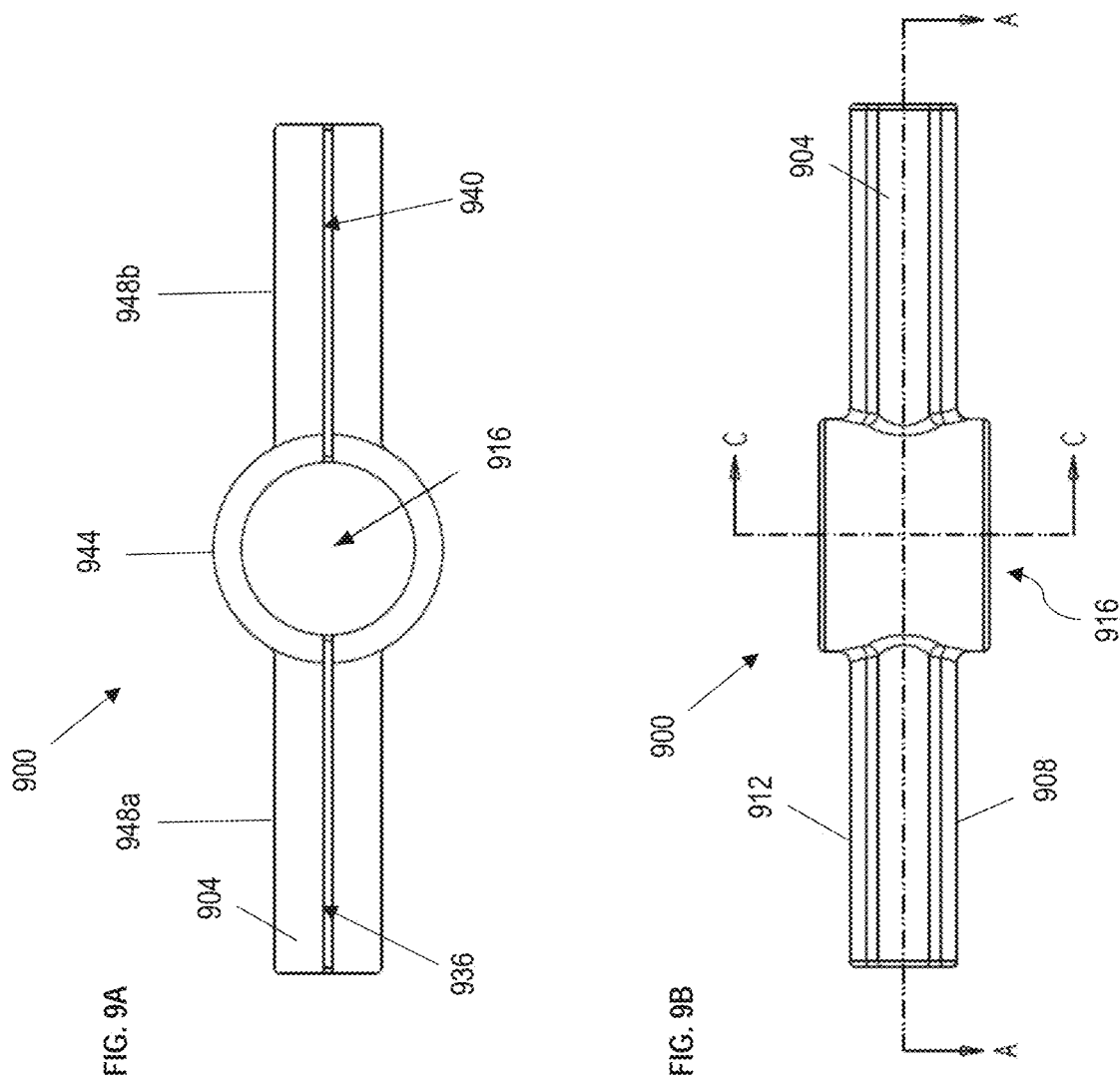

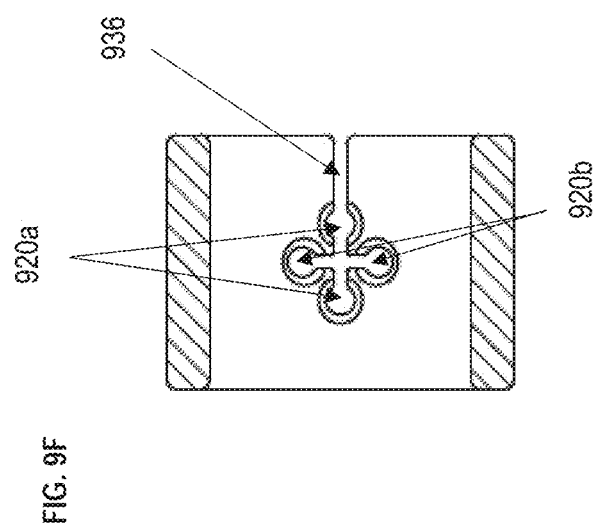
FIG. 9F
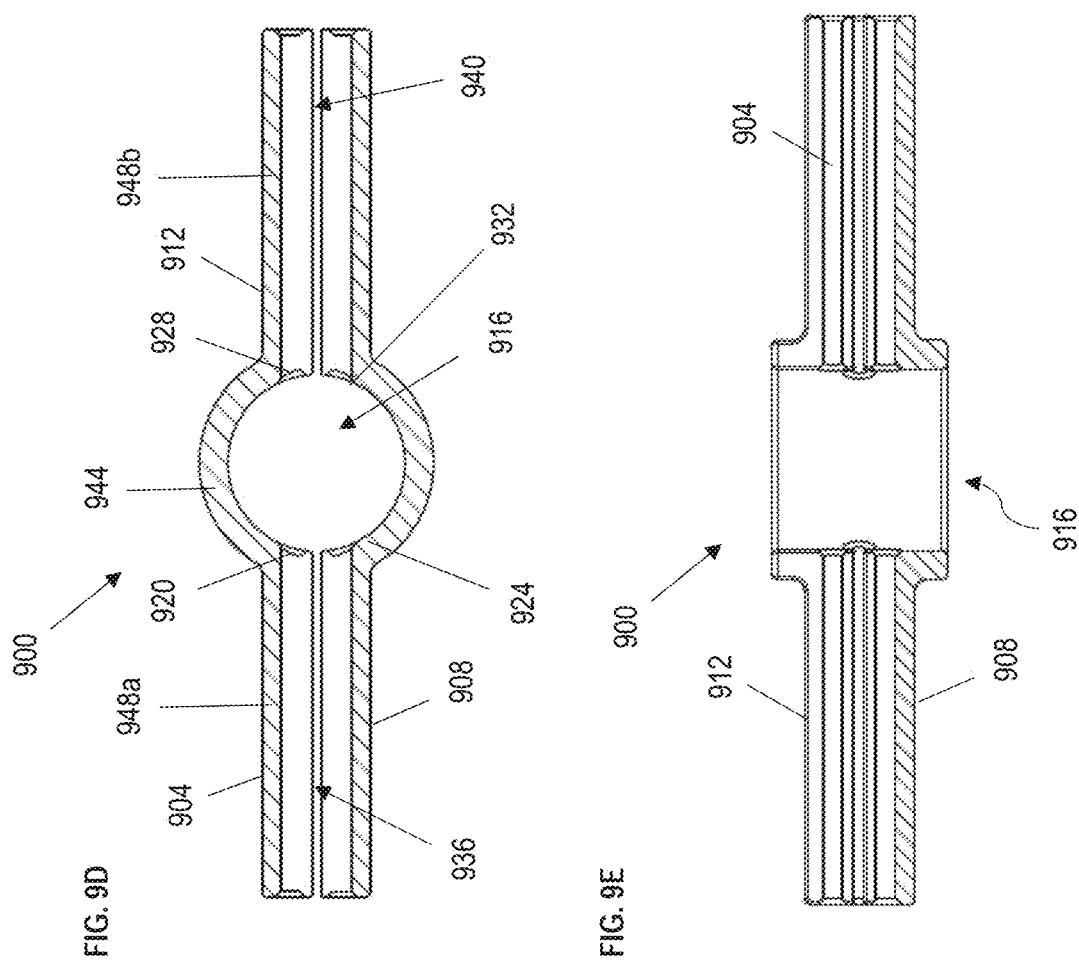
FIG. 9D
FIG. 9E

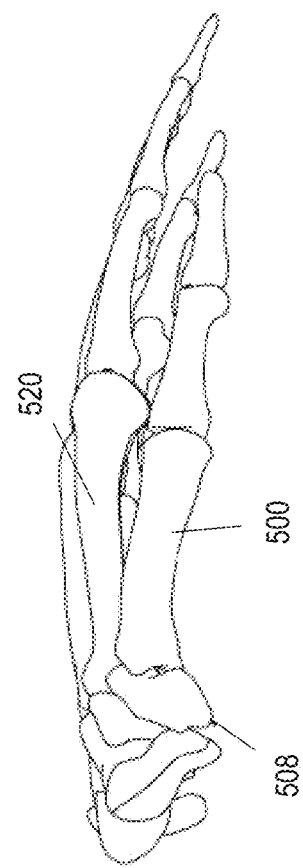
FIG. 11B
FIG. 11C
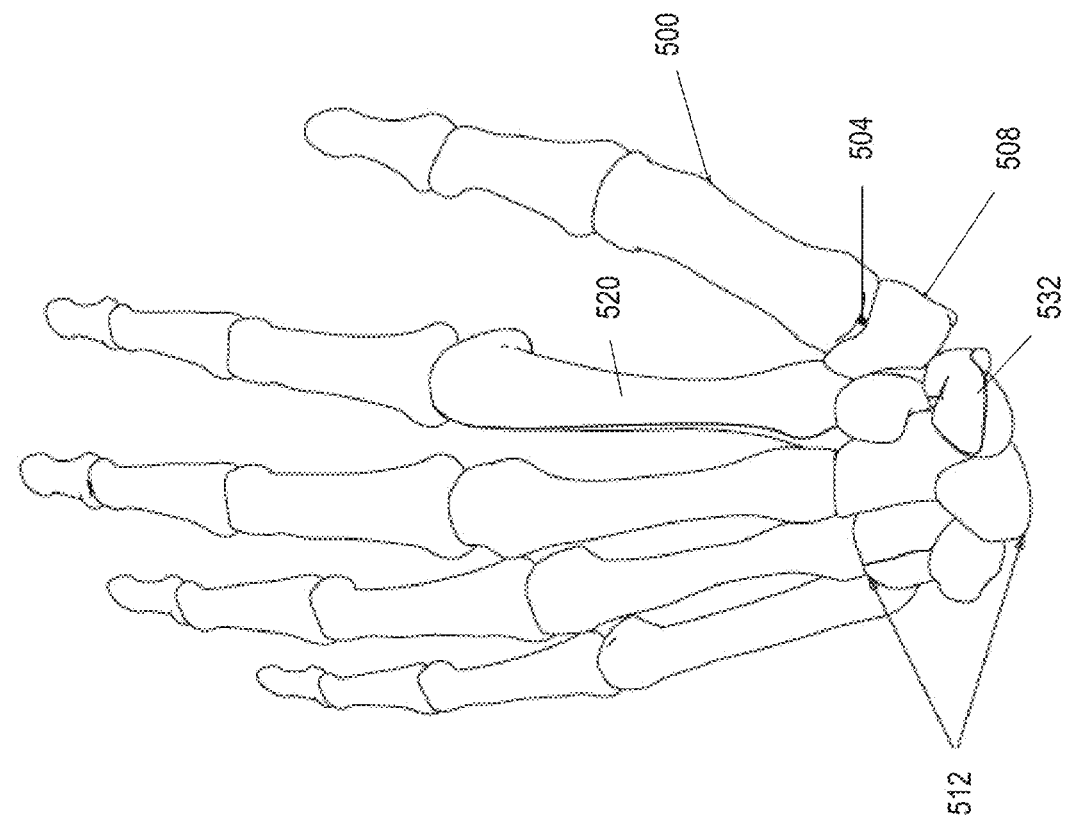
FIG. 11A

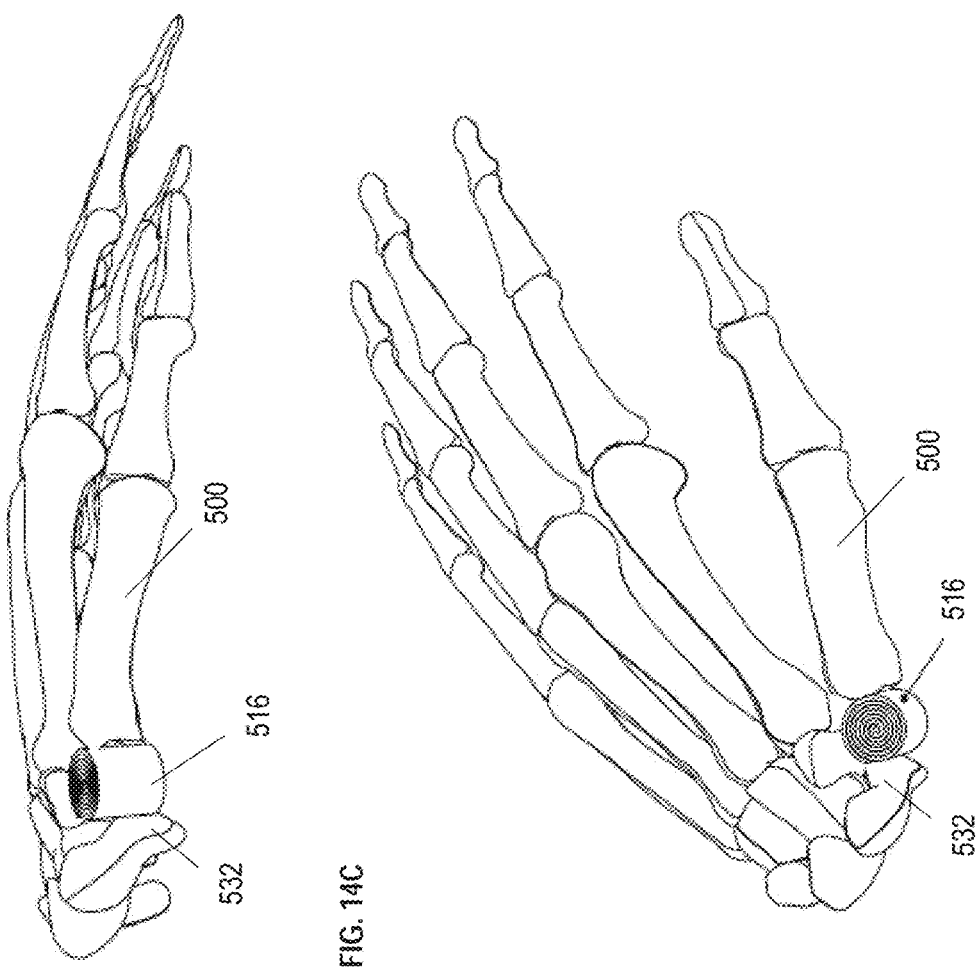
FIG. 14A
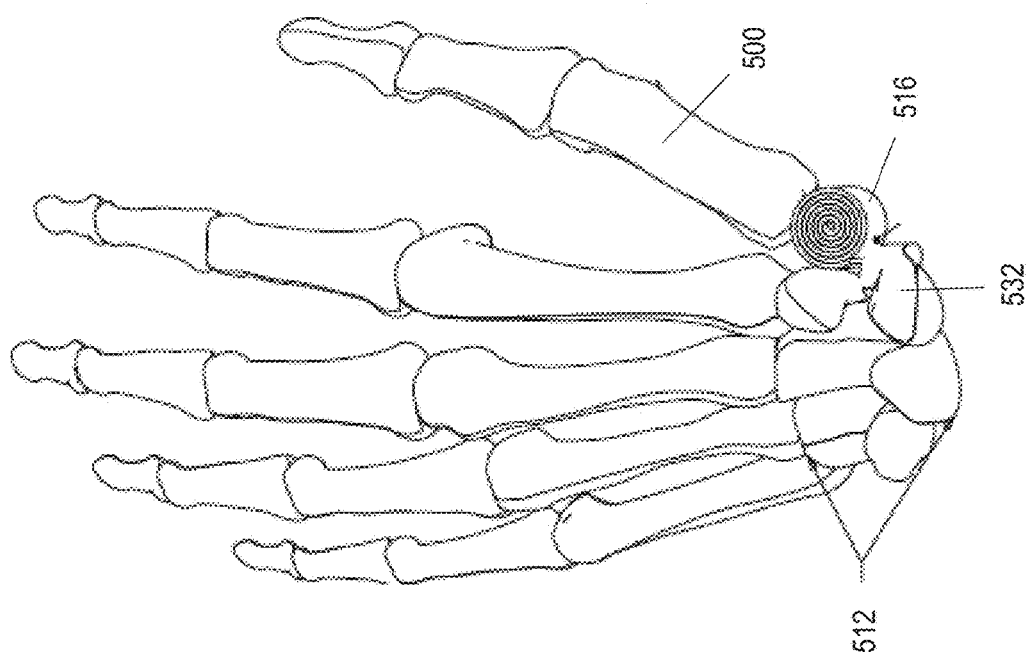
FIG. 14B
FIG. 14C

SYSTEMS AND METHODS FOR SIZING AND INTRODUCTION OF SOFT-TISSUE ALLOGRAFTS

CROSS-REFERENCE TO RELATED APPLICATIONS

This application claims the benefit of priority to U.S. Provisional Patent Application Ser. No. 62/687,901, filed Jun. 21, 2018, hereby incorporated by reference in its entirety.

TECHNICAL FIELD

The present application relates generally to systems and methods for a medical procedure involving soft-tissue allografts (e.g., dermal allograft) for the correction of skeletal impairment (e.g., misalignment, arthritis, etc.), and more particularly, but not by way of limitation, to sizers and delivery devices for introduction of such allografts.

BACKGROUND

Examples of sizers and delivery devices that can be used for introduction of tissue implants are disclosed in U.S. Pat. No. 6,168,631 (the '631 patent). Another example of an implant assembly is disclosed in U.S. Pat. No. 8,092,547 (the '547 patent). An example of an implant for correction of skeletal misalignment is disclosed in U.S. Pat. No. 4,450,591 (the '591 patent). Another example of a tissue implant is disclosed in U.S. Patent Application No. 2017/0189197 (the '197 Publication).

One example of a skeletal impairment condition is a fallen arch or "flatfoot." The condition involves a deformity in which the arches of the foot collapse, resulting in the entire sole of the foot being in complete or nearly complete contact with the ground. This may eventually cause other biomechanical issues with the physiology of the foot that, in turn, may adversely affect other parts of the body. The "flatfoot" condition occurs when the head of the talus bone is displaced medially and distally from the navicular bone, which in turn causes lateral misalignment throughout the foot as the talus and navicular bones tend to move outward. Furthermore, there is a change in relative alignment in the subtalar joint that occurs at the meeting point between the talus bone and the calcaneus bone such that the canal, which should naturally occur between the talus and calcaneus bones, is depressed. This canal is commonly referred to as the sinus tarsi. The misalignment of the talus and calcaneus bones eventually leads to misalignment of other bones in the foot and leg.

Another example of a skeletal impairment condition is osteoarthritis of the carpometacarpal (CMC) joint. The CMC joint is where the saddle-shaped trapezium bone articulates with the first metacarpal bone. An osteoarthritic CMC joint can become painful enough to severely limit activities of daily life for a large portion of the population. While symptoms may be treated with physical therapy, rest and stabilization, or anti-inflammatory medications, surgical intervention may be clinically indicated if pain persists. Interpositional arthroplasty of the CMC joint is the most common surgical procedure to treat osteoarthritis of the CMC joint.

Surgical intervention to treat osteoarthritis of the CMC joint begins with removal of a portion or all of the trapezium bone to create a void. To prevent complete collapse of the first metacarpal bone into the void created, a wire pin is used as a temporary stabilizer to align the base of the first metacarpal bone with the base of the index metacarpal. The flexor carpi radialis (FCP) tendon is then harvested, rolled up and sutured to prevent unrolling, and is interposed between the base of the thumb metacarpal and the scaphoid, the space previously occupied by the trapezium bone. In some cases, an additional procedure called a suspensionplasty is performed, where another piece of tendon is used to tie the base of the thumb metacarpal to the base of the index metacarpal.

While the outcomes of interpositional arthroplasty of the CMC joint are acceptable, there are several disadvantages to the procedure, such as additional trauma to the patient in taking an autograft, morbidity associated with the graft donor site, and inadequate amount or inadequate quality of tendon available. The time it takes to harvest an FCP tendon graft is not insignificant, and can be increased even more if suspensionplasty is added as an additional procedure. Additionally, there is evidence that during healing, the tendon graft weakens and loses structural strength, necessitating the use of pins to help hold the thumb metacarpal in the right position while dense scar tissue forms to support the metacarpal.

Prosthetic material, such as silicone rubber, has also been used to treat osteoarthritic CMC joints. However, all of these silicone rubber devices are subject to dislocation, fracture, abrasion and fatigue, which leads to the generation of small silicone particulate debris that cause a chronic inflammatory reaction called "silicone synovitis."

To address subtalar joint impairments, it has been discovered that by re-establishing the relative alignment between the talus and calcaneus bones, the overall arch structure of the foot can be reestablished as well. While this can be demonstrated by physically manipulating a person's foot, such physical manipulation is impractical during normal use of one's foot. As such, there have been various efforts made to provide implants which operate to physically reposition and realign the talus and calcaneus bones. However, like other prior art systems, apparatuses, and methods for sizing and introducing implants to correct skeletal impairments, the systems, apparatuses, and methods disclosed in the '631 patent, the '547 patent, the '591 patent, and '197 Publication, make it exceedingly difficult to simplify the surgical procedure for delivering a tissue implant and maintaining natural motion of the bones after correcting the impairment. Hence, there is a need for a system and method for overcoming one or more of the above identified challenges.

SUMMARY

This disclosure includes configurations of devices, apparatuses, kits, and methods for sizing and introducing soft-tissue allografts for treatment or correction of skeletal impairments. Non-limiting examples of surgical procedures that benefit from the present disclosure include, but are not limited to: subtalar joint arthroplasty; carpometacarpal joint arthroplasty; lateral mid-foot interpositional arthroplasty (e.g., $4^{th}/5^{th}$ metatarsal-cuboid joint); ankle interpositional arthroplasty (e.g., tibio-talar joint); elbow interpositional arthroplasty (e.g., radio-capitellar joint); proximal femoral interpositional arthroplasty; and interphalangeal interpositional arthroplasty (e.g., proximal interphalangeal joints of the fingers). For example, at least some of the present configurations include a trial sizer comprising an elongated shaft having a proximal end and a distal end, and a radiopaque tip coupled to the distal end of the elongated shaft, the tip having a transverse dimension equal to or greater than a corresponding transverse dimension of the elongated shaft, and having dimensions that mimic the dimensions of a corresponding soft-tissue allograft. In this way, at least some configurations of the present apparatuses can aid in determining the appropriate size and location of the soft-tissue allograft appropriate for transplantation at the site of delivery in a way that has previously not been possible with prior art trial sizers.

Some configurations of the present trial sizers comprise: an elongated shaft having a proximal end and a distal end; and a radiopaque tip coupled to the distal end of the elongated shaft, the tip having a transverse dimension equal to or greater than a corresponding transverse dimension of the elongated shaft, and having dimensions that mimic the dimensions of a corresponding soft-tissue allograft.

In some configurations of the present trial sizers, the elongated shaft defines a channel extending between and through the proximal and distal ends of the elongated shaft. In some configurations of the present trial sizers, the elongated shaft is configured to indicate insertion depth. In some configurations of the present trial sizers, the distal end of the elongated shaft comprises a plurality of indicia to indicate insertion depth. In some configurations of the present trial sizers, the distal end of the elongated shaft defines one or more threads along a portion of a length of the distal end.

In some configurations of the present trial sizers, the trial sizer further includes a trial sizer head defining a channel extending between, and through, a proximal end to a distal end, the trial sizer head being coupled to the proximal end of the elongated shaft. In some configurations of the present trial sizers, the trial sizer head is unitary with the elongated shaft.

In some configurations of the present trial sizers, the radiopaque tip can be uncoupled from the distal end of the elongated shaft and the elongated shaft can be used to push an implant through the delivery cannula to an insertion point. In some configurations of the present trial sizers, the length of the radiopaque tip is from 8 mm to 25 mm.

Some configurations of the present kits comprise: a configuration of the present trial sizers, and a delivery cannula comprising: an elongated body having a proximal end and a distal end, and defining a longitudinal channel extending between and through the proximal and distal ends; and a handle portion coupled to the proximal end of the elongated body, the handle portion defining a channel that is aligned with the longitudinal channel of the elongated body.

In some configurations of the present kits, the elongated shaft defines a channel extending between and through the proximal and distal ends of the elongated shaft. In some configurations of the present kits, the elongated shaft is configured to indicate insertion depth. In some configurations of the present kits, the distal end of the elongated shaft comprises a plurality of indicia to indicate insertion depth. In some configurations of the present kits, the elongated shaft defines one or more threads along a portion of its length closer to the distal end than to the proximal end.

In some configurations of the present kits, the kit further comprises a trial sizer head defining a channel extending between, and through, a proximal end to a distal end, the trial sizer head being coupled to the proximal end of the elongated shaft. In some configurations of the present kits, the trial sizer head is unitary with the elongated shaft of the trial sizer.

In some configurations of the present kits, the radiopaque tip can be uncoupled from the distal end of the elongated shaft and the elongated shaft can be used to push an implant through the delivery cannula to an insertion point. In some configurations of the present kits, the length of the radiopaque tip is from 8 mm to 25 mm.

In some configurations of the present kits, the elongated body of the delivery cannula comprises transparent material.

In some configurations of the present kits, the kit further comprises a delivery tool comprising an elongated shaft having a proximal end and a distal end that is configured to indicate insertion depth. In some configurations of the present kits, the distal end of the elongated shaft comprises a plurality of indicia to indicate insertion depth. In some configurations of the present kits, the elongated shaft of the delivery tool has a diameter from 5 mm to 15 mm. In some configurations of the present kits, the delivery tool further comprises a delivery tool head coupled to the proximal end of the elongated shaft. In some configurations of the present kits, the delivery tool head is unitary with the elongated shaft.

In some configurations of the present kits, the elongated shaft of the trial sizer is configured to have an outer diameter from 5 mm to 15 mm. In some configurations of the present kits, the delivery cannula is configured to have an inner diameter from 5 mm to 15 mm.

In some configurations of the present kits, a distal end of the trial sizer head has a first portion with a first transverse dimension, and a second portion with a second transverse dimension larger than the first transverse dimension, the first transverse dimension being larger than a corresponding transverse dimension of the channel of the delivery cannula to prevent the first portion from entering the channel of the delivery cannula.

In some configurations of the present kits, the kit further comprises at least one sterile dermal allograft having a diameter about equal to an average width of a canal between a subject's misaligned bones, where the dermal allograft implant is compressible and flexible. In some configurations of the present kits, the dermal allograft has a density sufficient to resist full compression of the canal.

In some configurations of the present kits, the kit further comprises a package within which the other components of the kit are sealed.

Some implementations of the present methods for sizing and delivering an implant comprise (a) disposing a delivery cannula through an incision in the skin of a patient such that a distal end of the delivery cannula is disposed between the incision and a given space between bones of the patient; (b) inserting a trial sizer of any of the presently disclosed kits or of the presently disclosed apparatuses into the space; (c) determining whether the trial sizer fits into the space in an acceptable way, and: (i) if the trial sizer fits into the space in an acceptable way, delivering an implant through the delivery cannula into the space; or (ii) if the trial sizer does not fit into the space in an acceptable way, sequentially repeating steps (b) and (c) with a trial sizer of a different size until a trial sizer fits into the space in an acceptable way.

Some implementations of the present methods for sizing and delivering an implant further comprise removing the delivery cannula after delivering the implant. In some implementations of the present methods for sizing and delivering an implant, the method further comprises suturing the incision closed.

In some implementations of the present methods for sizing and delivering an implant, the delivery cannula comprises an elongated body having a proximal end and a distal end, and defining a longitudinal channel extending between, and through, the proximal end and the distal end, and a handle portion coupled to the proximal end of the elongated body, the handle portion defining a channel that is aligned with and in fluid communication with the longitudinal channel of the elongated body.

In some implementations of the present methods for sizing and delivering a soft-tissue allograft, the method further comprises inserting a delivery tool comprising an elongated shaft having a proximal end and a distal end, where the distal end of the elongated shaft is configured to indicate insertion depth.

In some configurations of the present trial sizers, a trial sizer comprises: a cylindrical head having a first side, a second side, and a peripheral surface extending between the first and second sides and defining a circular cross sectional shape of the head; a handle having a proximal end and a distal end coupled to the peripheral surface; and where the head has dimensions that mimic the dimensions of a corresponding implant.

In some configurations of the present trial sizers, the head is radiopaque. In some configurations, the head is unitary with the handle. In some configurations, a transverse dimension of the head is from 5 mm to 25 mm.

In some configurations of the present suture delivery guides, a suture delivery guide comprises: a body having a first side and a second side and defining an implant chamber extending through the first side toward the second side, the body defining a plurality of first suture passages on a first side of the implant chamber and a plurality of second suture passages on a second side of the implant chamber, each of the second suture passages being aligned with a corresponding one of the first suture passages, the body further defining a first slot extending through the first side of the body and in fluid communication with all of the first suture passages, and a second slot extending through the first side of the body and in fluid communication with all of the second suture passages.

In some configurations of the present suture delivery guides, the body has a medial portion defining the implant chamber and two lateral portions on opposite sides of the medial portion, a first one of the lateral portions defining the first suture passages, and a second one of the lateral portions defining the second suture passages.

In some configurations of the present suture delivery guides, each of two of the first suture passages and a corresponding each of two of the second suture passages is intersected by a reference plane that extends parallel to the first and second slots and through the first and second sides of the body.

In some configurations of the present suture delivery guides, a set of two of the first suture passages and a corresponding set of two of the second suture passages is arranged relative to a reference plane that extends parallel to the first and second slots and through the first and second sides of the body, such that the two first suture passages are disposed on opposite sides of the plane, and the two second suture passages are disposed on opposite sides of the plane.

In some configurations of the present kits, a kit comprises: at least one of a configuration of any of the presently disclosed trial sizers; and at least one of a configuration of any of the presently disclosed suture delivery guides.

In some configurations of the present kits, the kit further comprises: at least one sterile dermal allograft having a diameter about equal to an average width of a canal between a subject's misaligned bones, where the dermal allograft is compressible and flexible.

In some configurations of the present kits, the dermal allograft has a density sufficient to resist full compression.

In some configurations of the present kits, the kit further comprises a package within which the other components of the kit are sealed.

In some implementations of the present methods, a method comprises: (a) inserting a trial sizer of any of the kits presently disclosed or any configuration of the trial sizers disclosed herein into a given space between bones of the patient; (b) determining whether the trial sizer fits into the space in an acceptable way, and (i) if the trial sizer fits into the space in an acceptable way, delivering an implant to the space; or (ii) if the trial sizer does not fit into the space in an acceptable way, sequentially repeating steps (b) and (c) with a trial sizer of a different size until a trial sizer fits into the space in an acceptable way.

In some implementations of the present methods, a bone (e.g., the trapezium bone) is excised prior to inserting the trial sizer.

In some implementations of the present methods, the peripheral surface of the head of the trial sizer faces bone.

In some implementations of the present methods, the first end and the second end of the head of the trial sizer faces bone.

In some implementations of the present methods, delivering an implant to the space comprises using a suture delivery guide. The suture delivery guide may include any configuration of the suture delivery guides presently disclosed.

In some implementations of the present methods, delivering a soft-tissue allograft to the space comprises: inserting a suture anchor in the distal aspect of the 2nd metacarpal bone; and fastening a soft-tissue allograft to the suture anchor.

In some implementations of the present methods, delivering a soft-tissue allograft to the space comprises: (a) passing a suture through a soft-tissue allograft and looping the suture through a flexor carpi radialis tendon; (b) looping the suture back through the soft-tissue allograft; (c) delivering the soft-tissue allograft over the suture and into the space between bones of the patient; and (d) tying the suture using an acceptable surgical knot.

In some implementations of the present methods, a method comprises: providing at least one sterile pre-formed soft-tissue allograft rod plug having a diameter about equal to an average width of a space between a person's bones and a density sufficient to resist full compression of the space, the pre-formed soft-tissue allograft rod plug being resiliently compressible and flexible while remaining substantially as the formed plug; and delivering the at least one sterile pre-formed soft-tissue allograft rod plug into the space between a set of bones of the patient, where the set of bones is selected from the group of sets of bones consisting of: (a) a $1^{st}$ metacarpal bone and a scaphoid bone; (b) a $4^{th}$ metatarsal bone, $5^{th}$ metatarsal bone, and cuboid bone; (c) a $5^{th}$ metatarsal bone; (d) a tibia bone and a talus bone; (e) a radius bone and a humerus bone; (f) a femur bone and a pelvis bone; (g) any of the proximal phalanges of a hand and any of the corresponding intermediate phalanges of a hand.

In some implementations of the present methods, a portion or all of a patient's trapezium bone is removed prior to delivering the at least one sterile dermal allograft.

In some implementations of the present methods, a trial sizer is inserted into the space created between the $1^{st}$ metacarpal and the scaphoid bone of the patient's hand prior to delivering the at least one sterile dermal allograft.

In some implementations of the present methods, the space is between the $4^{th}$ and $5^{th}$ metatarsal bones of the foot and the cuboid bone of the foot.

In some implementations of the present methods, the space is between a tibia bone and a talus bone of the patient.

In some implementations of the present methods, the space is between a radius bone and a capitellum portion of a humerus bone of the patient.

In some implementations of the present methods, the space is between a femur bone and a pelvis bone of the patient.

In some implementations of the present methods, the space is between any of the proximal phalanges of a hand and any of the corresponding intermediate phalanges of a hand.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any configuration or implementation of the present devices, apparatuses, kits, and methods, the term "substantially" may be substituted with "within [a percentage] of" what is specified, where the percentage includes 0.1, 1, 5, and/or 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus or kit that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Further, an apparatus, device, or structure that is configured in a certain way is configured in at least that way, but it can also be configured in other ways than those specifically described.

Any configuration or implementation of any of the present devices, apparatuses, kits, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the configurations described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the configurations depicted in the figures.

FIG. 1A shows a side view of a configuration of the present trial sizers.

FIG. 1B shows a cross-sectional side view of the trial sizer of FIG. 1A taken along a plane bisecting the elongated shaft extending from the trial sizer head to the tip.

FIG. 6 shows a flow chart for depicting a process for sizing and delivering a tissue implant using a configuration of a trial sizer of any of the presently disclosed kits or presently disclosed apparatuses.

FIGS. 7F-7P shows top and isometric views of a patient's foot during a subtalar operation for sizing and delivering a tissue implant using an apparatus of the present invention.

FIG. 8B-8D shows an isometric, side, and cross-sectional view of a head of the trial sizer of FIG. 8A.

FIG. 9A shows a side view of a configuration of the present suture delivery guides.

FIG. 9B shows a top view of the suture delivery guide of FIG. 9A.

FIG. 9C shows a cross-sectional view of the suture passages disposed within the suture delivery guide of FIG. 9A and taken along a plane bisecting the suture delivery guide.

FIG. 9D shows a cross-sectional side view of the suture delivery guide of FIG. 9A taken along a plane bisecting the longitudinal dimension of the suture delivery guide.

FIG. 9E shows a cross-sectional top view of the suture delivery guide of FIG. 9D.

FIG. 9F shows a cross-sectional view of the suture passages on a side of the allograft chamber and taken along a plane bisecting the suture delivery guide.

FIG. 11A shows a top view of the thumb metacarpal bone, carpometacarpal joint, trapezium, and carpal bones of the hand.

FIG. 11B shows a sagittal view of the hand bones of FIG. 11A.

FIG. 11C shows an isometric view of the hand bones of FIG. 11A.

FIG. 14A shows a top view of the hand bones with an allograft disposed in a first orientation similar to the orientation of the trial sizer in FIG. 12A.

FIG. 14B shows a sagittal view of FIG. 14A.

FIG. 14C shows an isometric view of FIG. 14A.

DESCRIPTION OF ILLUSTRATIVE EMBODIMENTS

Figure 2B:
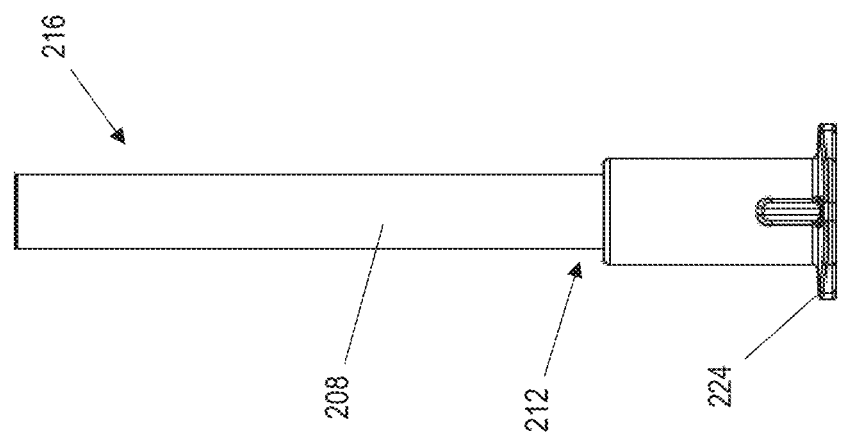
FIG. 2B shows a side view of the delivery cannula of FIG. 2A.
Figure 2A:
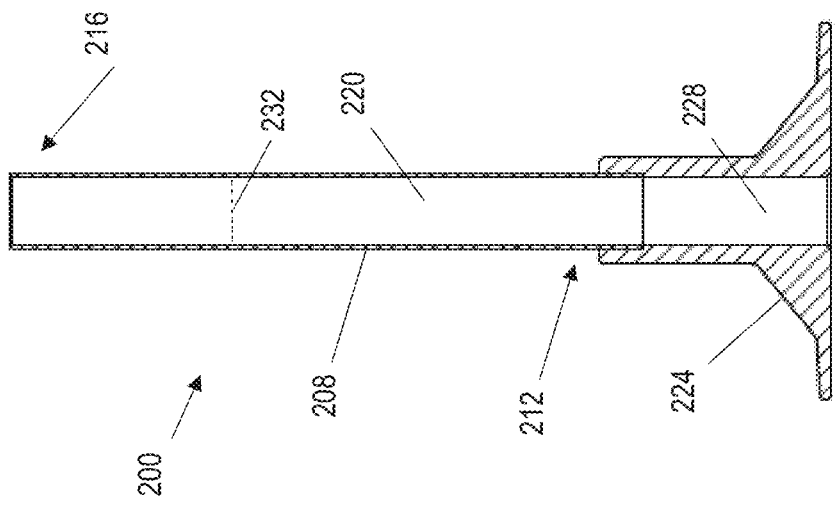
FIG. 2A shows a cross-sectional side view of a configuration of the delivery cannula of the present kits taken along a plane bisecting the elongated body extending from the proximal end to the distal end of the delivery cannula.
Figure 2C:
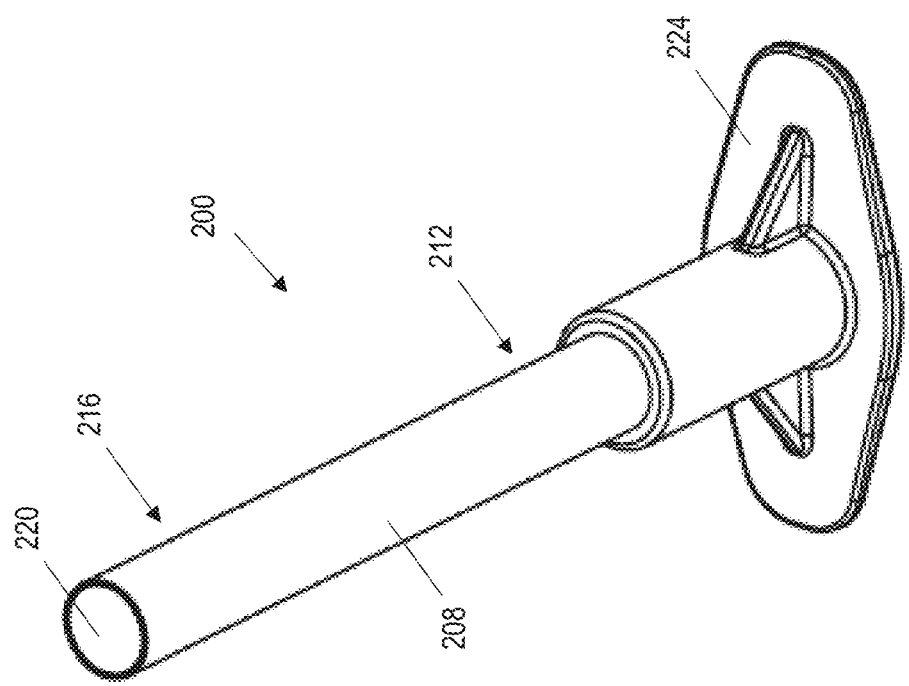
FIG. 2C shows an isometric view of the delivery cannula of FIGS. 2A-2B.
Figure 3B:
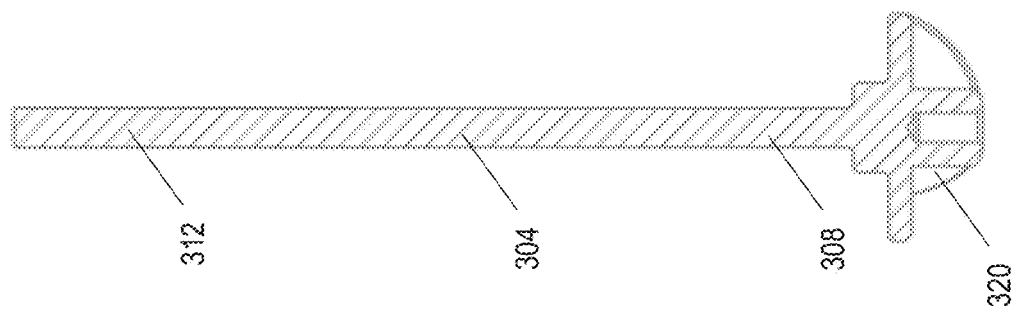
FIG. 3B shows a cross-sectional side view of the delivery tool of FIG. 3A taken along a plane bisecting the elongated shaft extending from the delivery tool head to the distal end of the delivery tool.
Figure 3A:
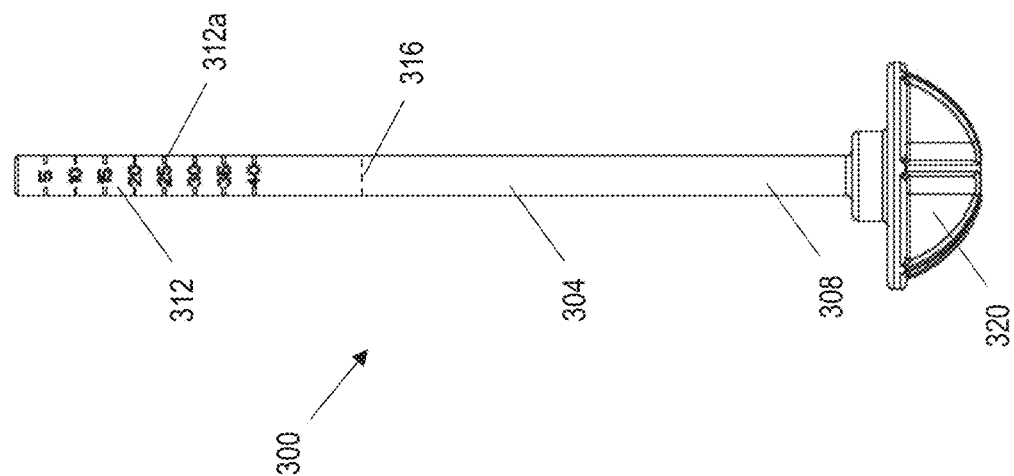
FIG. 3A shows a side view of a configuration of the delivery tool of the present kits.
Figure 3C:
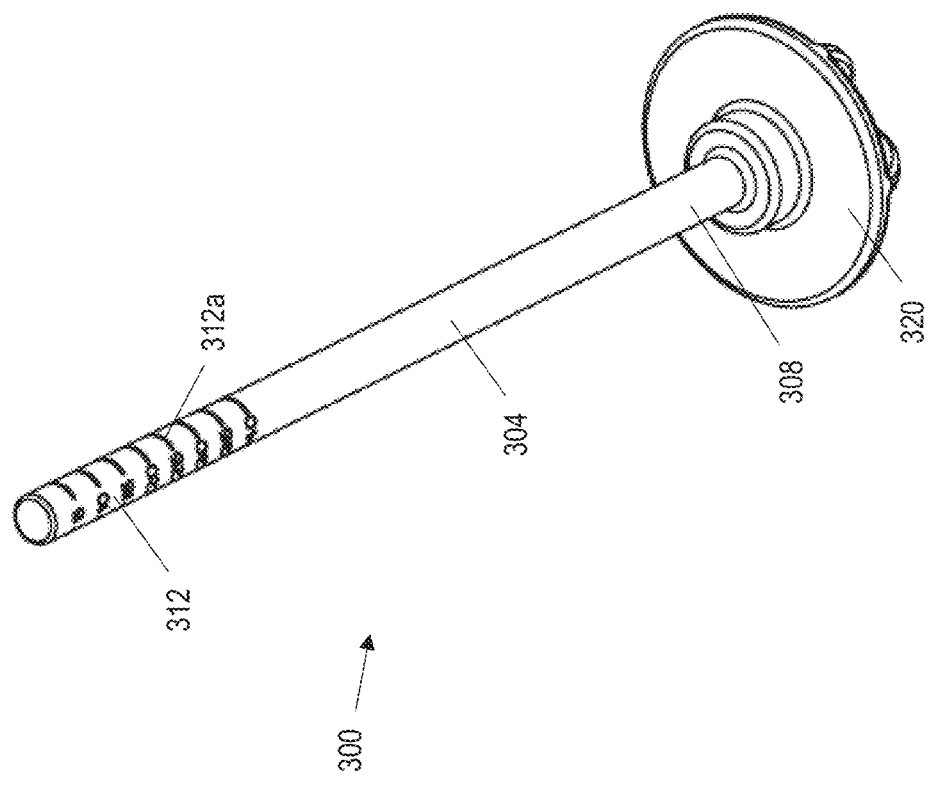
FIG. 3C shows an isometric view of the delivery tool of FIGS. 3A-3B.
Figure 4:
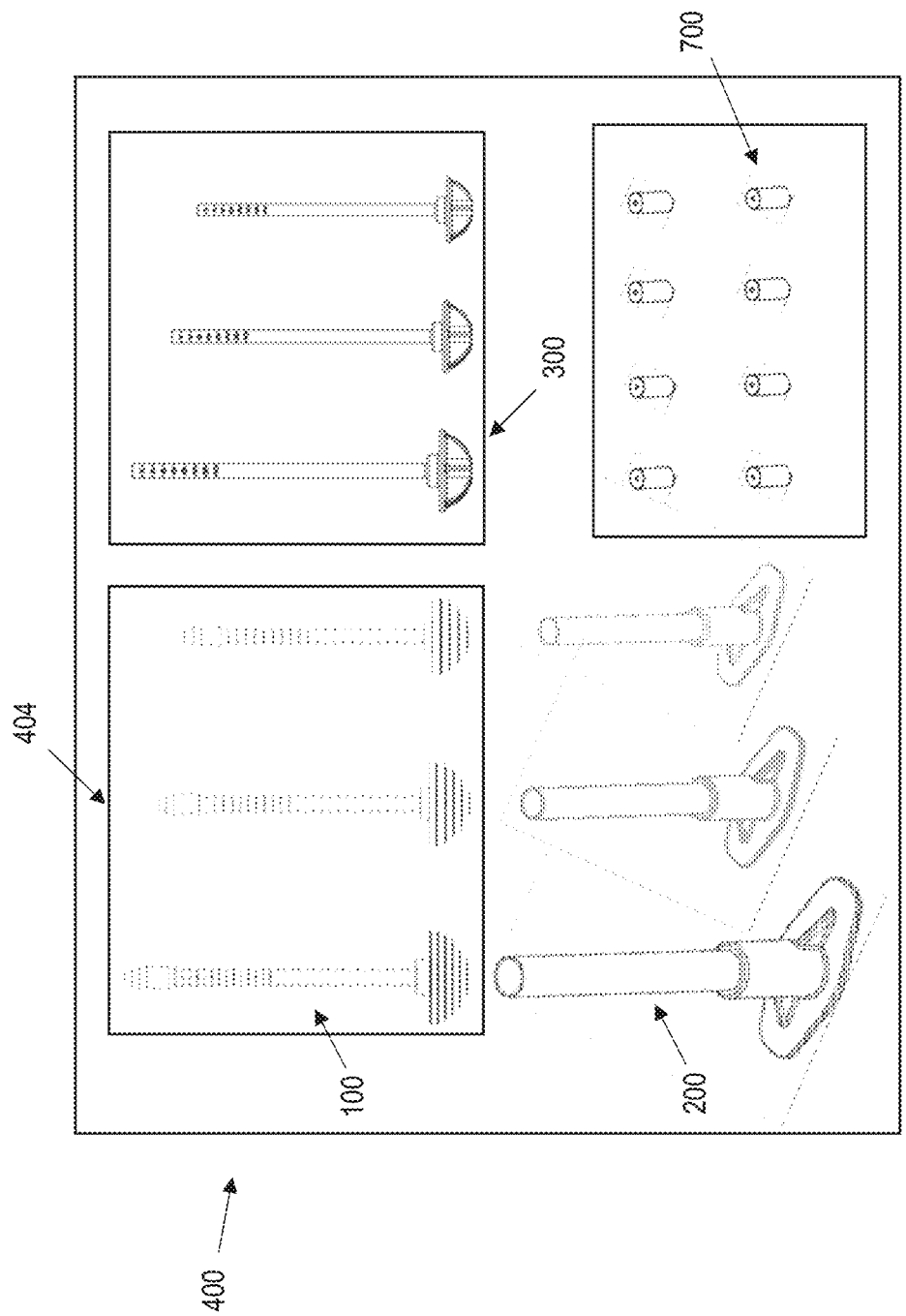
FIG. 4 shows a top view of a configuration of the present kits containing various sizes of trial sizers, delivery cannulas, and delivery tools, where the trial sizers and delivery tools are separately packaged within the sterile kit.
Figure 7A:
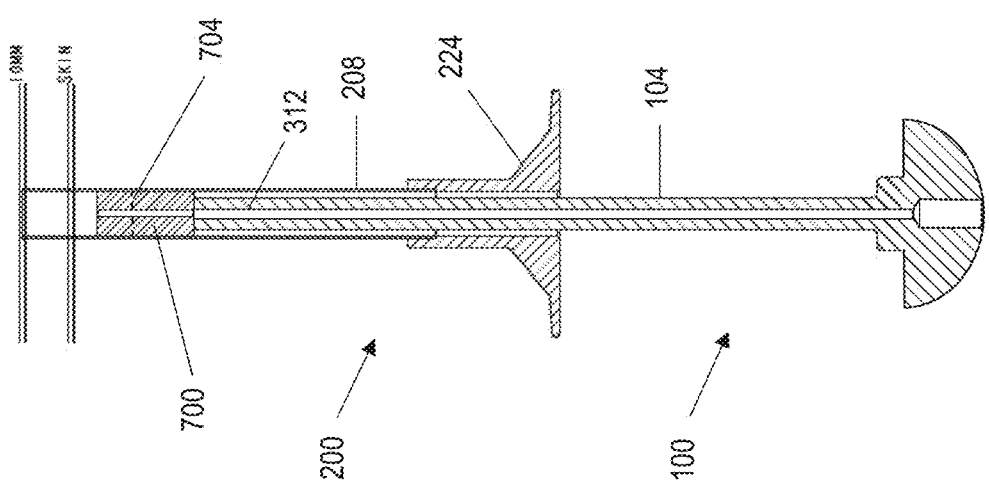
FIG. 7A shows a cross-sectional view of the delivery cannula, inserted to a point at least 10 mm beneath the skin surface, with a dermal allograft implant at the distal end of the elongated shaft of the trial sizer that is inserted in the channel of the delivery cannula.
Figure 7B:
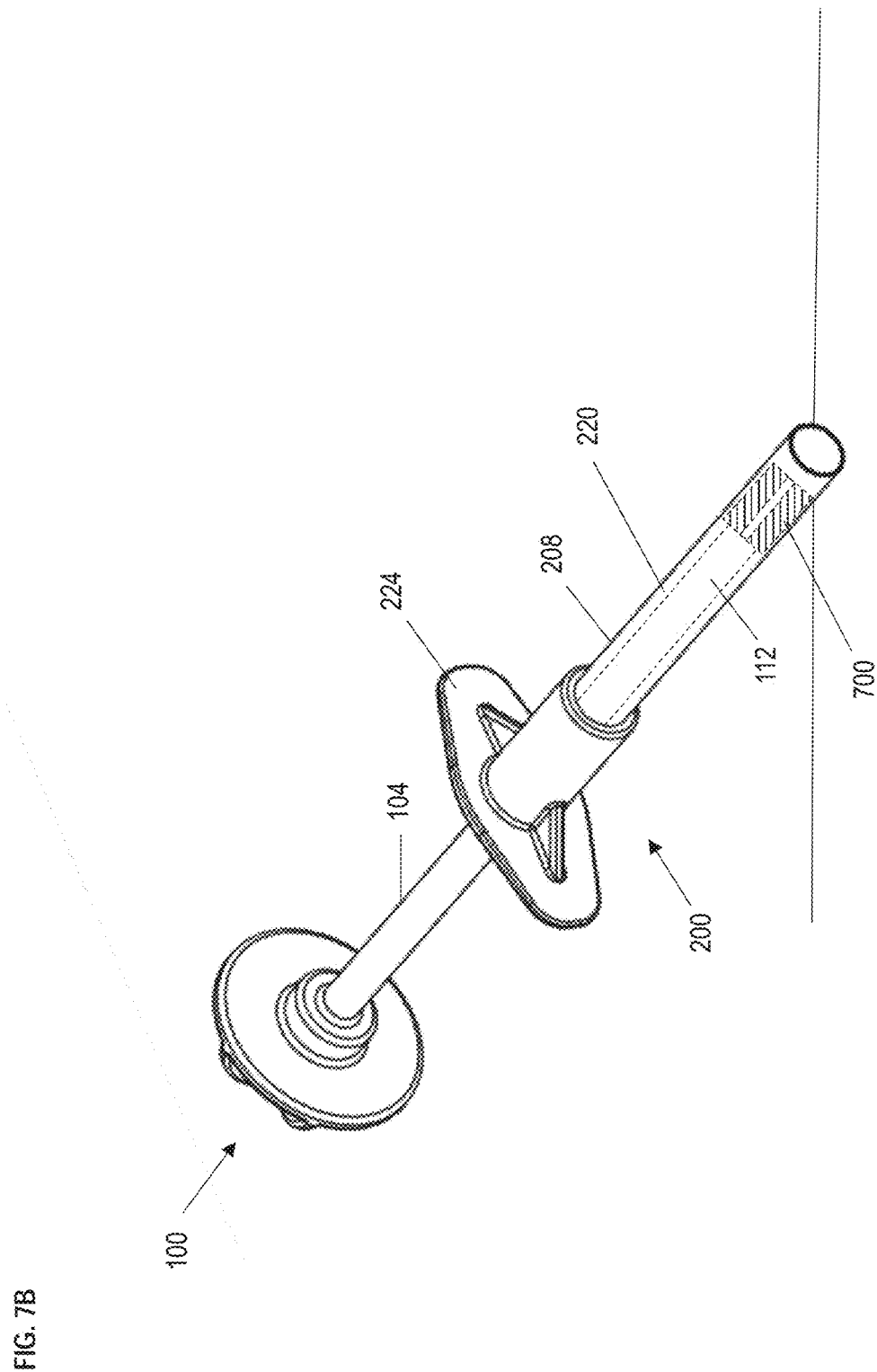
FIG. 7B shows an isometric view of FIG. 7A.
Figure 7D:
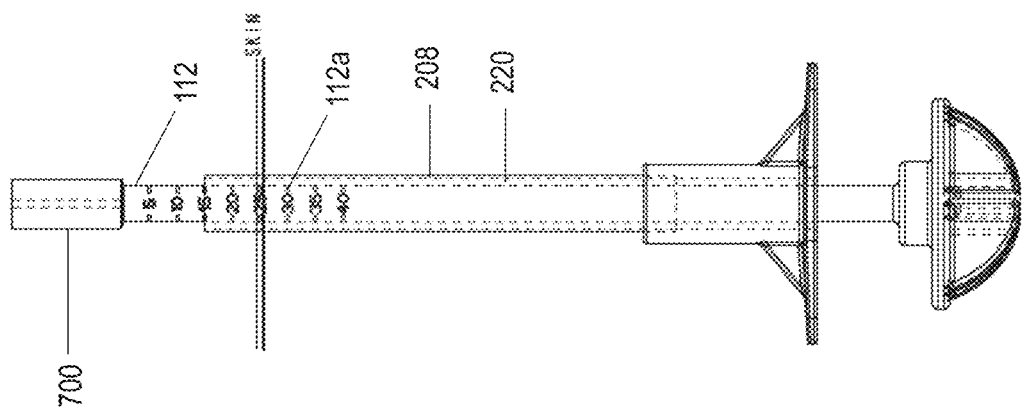
FIG. 7D shows a side view of the apparatus of FIG. 7C, depicting the trial sizer pushing the dermal allograft implant to a depth of 25 mm beneath the skin surface.
Figure 7C:
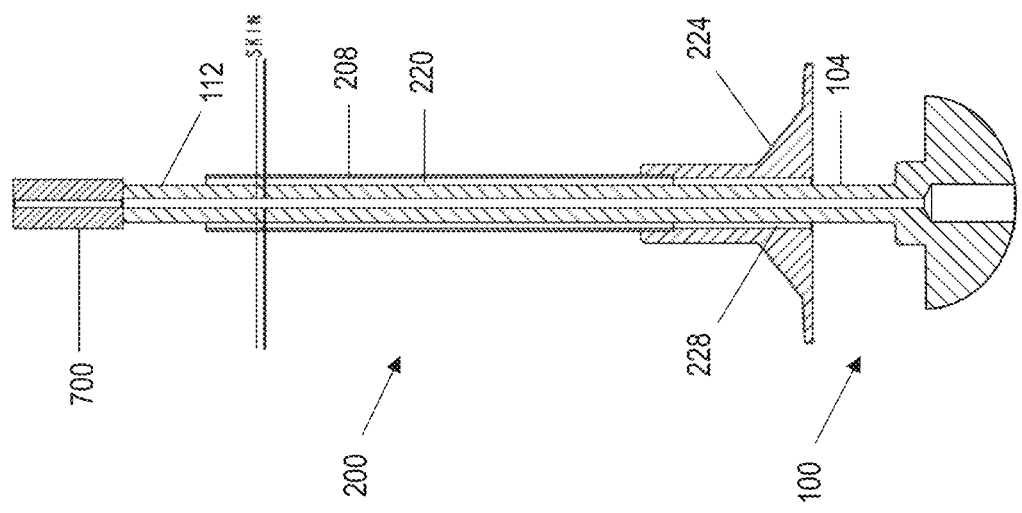
FIG. 7C shows a cross-sectional view of the apparatus of FIG. 7A, with the trial sizer pushing the dermal allograft implant beyond the distal end of the delivery cannula inserted beneath the skin surface.
Figure 7E:
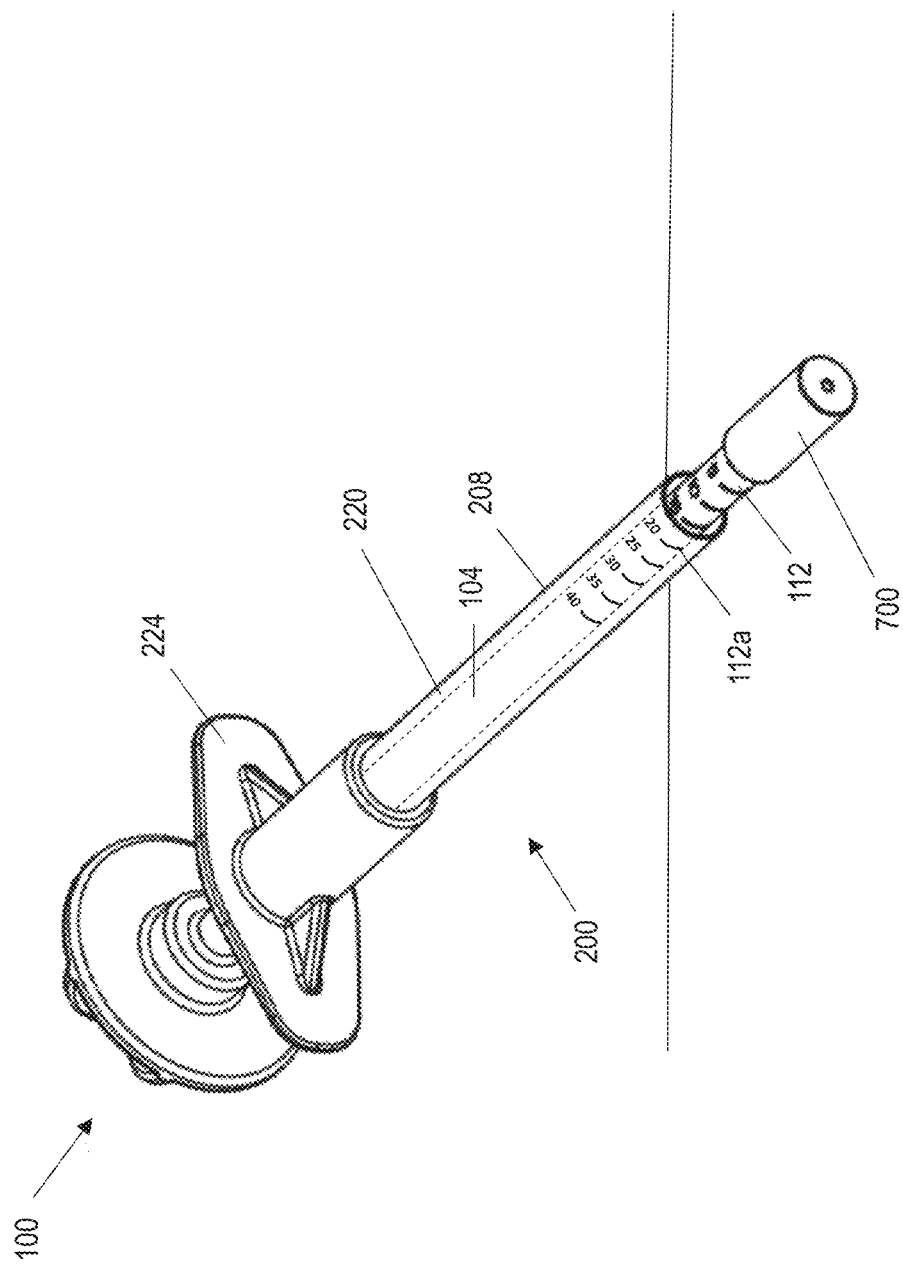
FIG. 7E shows an isometric view of the apparatus of FIGS. 7C-7D.
Figure 7P:
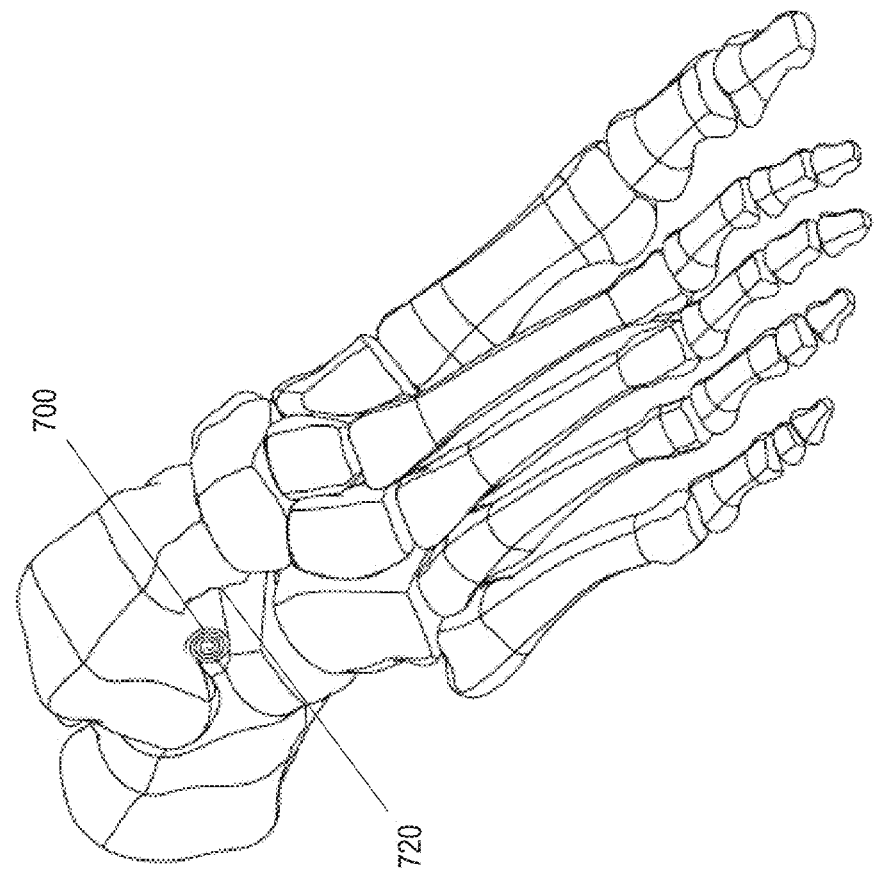

Referring now to the drawings, and more particularly to FIGS. 1A-7E, FIG. 1A shows a side view of a configuration of the present trial sizers; FIG. 1B shows a cross-sectional side view of the trial sizer of FIG. 1A taken along a plane bisecting the elongated shaft extending from the trial sizer head to the tip; FIG. 1C shows an isometric view of the trial sizer of FIGS. 1A, 1B; FIG. 1D shows a side view of the trial sizer of FIGS. 1A-1C inserted into an incision in skin to an insertion point located 25 mm below the skin surface; FIG. 2A shows a cross-sectional side view of a configuration of the delivery cannula of the present kits taken along a plane bisecting the elongated body extending from the proximal end to the distal end of the delivery cannula; FIG. 2B shows a side view of the delivery cannula of FIG. 2A; FIG. 2C shows an isometric view of the delivery cannula of FIGS. 2A-2B; FIG. 3A shows a side view of a configuration of the delivery tool of the present kits; FIG. 3B shows a cross-sectional side view of the delivery tool of FIG. 3A taken along a plane bisecting the elongated shaft extending from the delivery tool head to the distal end of the delivery tool; FIG. 3C shows an isometric view of the delivery tool of FIGS. 3A-3B; FIG. 4 shows a top view of a configuration of the present kits containing various sizes of trial sizers, delivery cannulas, and delivery tools, where the trial sizers and delivery tools are separately packaged within the sterile kit; FIG. 5A shows a cross-sectional view of a configuration of the present trial sizers inserted into a configuration of the present delivery cannula, with the tip of the trial sizer extending past the distal end of the delivery cannula at least 10 mm, with the distal end of the delivery cannula located at least 10 mm beneath the skin surface; FIG. 5B shows an isometric view of the apparatus of FIG. 5A, with a portion of the tip of the trial sizer extending past the distal end of the delivery cannula; FIG. 6 shows a flow chart for depicting a process for sizing and delivering a soft-tissue allograft using a configuration of a trial sizer of any of the presently disclosed kits or presently disclosed apparatuses; FIG. 7A shows a cross-sectional view of the delivery cannula, inserted to a point at least 10 mm beneath the skin surface, with a dermal allograft at the distal end of the elongated shaft of the delivery tool that is inserted in the channel of the delivery cannula; FIG. 7B shows an isometric view of FIG. 7A; FIG. 7C shows a cross-sectional view of the apparatus of FIG. 7A, with the delivery tool pushing the dermal allograft beyond the distal end of the delivery cannula inserted beneath the skin surface; FIG. 7D shows a side view of the apparatus of FIG. 7C, depicting the delivery tool pushing the dermal allograft to a depth of 25 mm beneath the skin surface; and FIG. 7E shows an isometric view of the apparatus of FIGS. 7C-7D.

In a particular configuration, such as the one shown in FIGS. 1A-1D, trial sizer 100 comprises: an elongated shaft 104 having a proximal end 108 and a distal end 112; and a radiopaque tip 116 coupled to distal end 112 of elongated shaft 104, where tip 116 has a transverse dimension 120 equal to or greater than a corresponding transverse dimension 124 of elongated shaft 104, and having dimensions that mimic the dimensions of a corresponding soft-tissue allograft (e.g., dermal allograft 700). For example, transverse dimension 120 may be equal to a transverse dimension of a soft-tissue allograft (e.g., dermal allograft 700) so that an operator may determine the dimensions of the allograft needed for a procedure before implanting the allograft, as described in greater detail below.

Figure 1C:
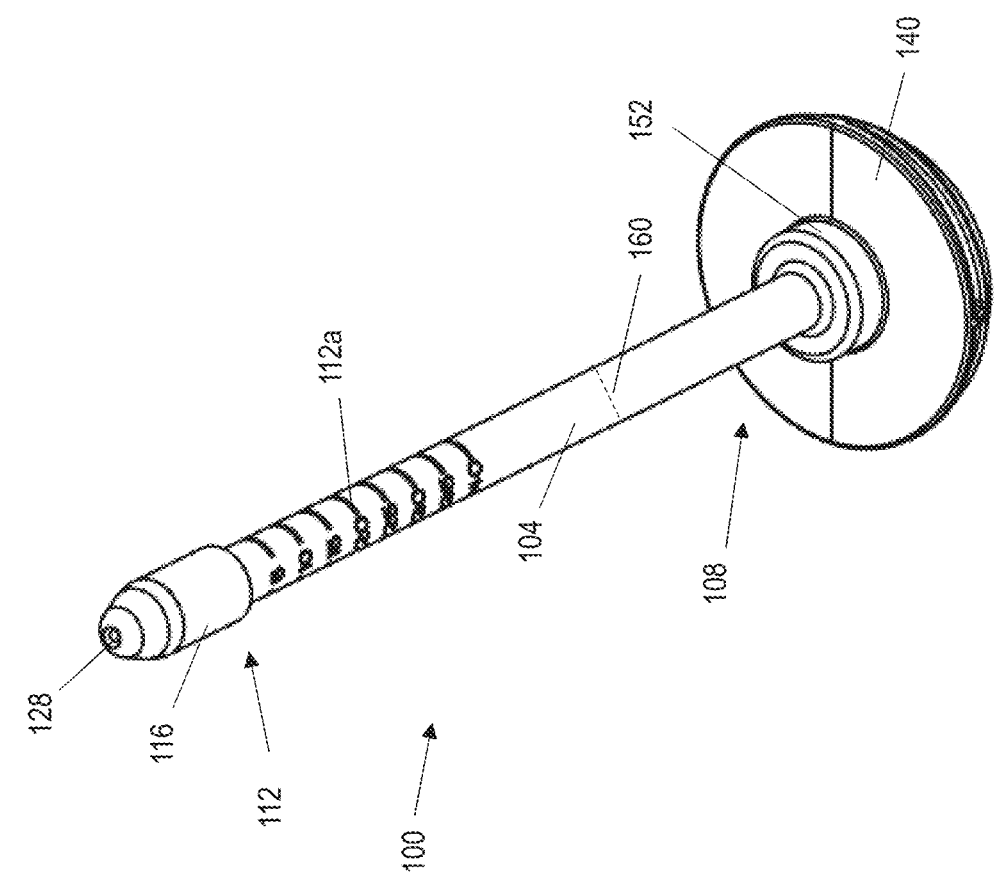
FIG. 1C shows an isometric view of the trial sizer of FIGS. 1A, 1B.
Figure 1D:
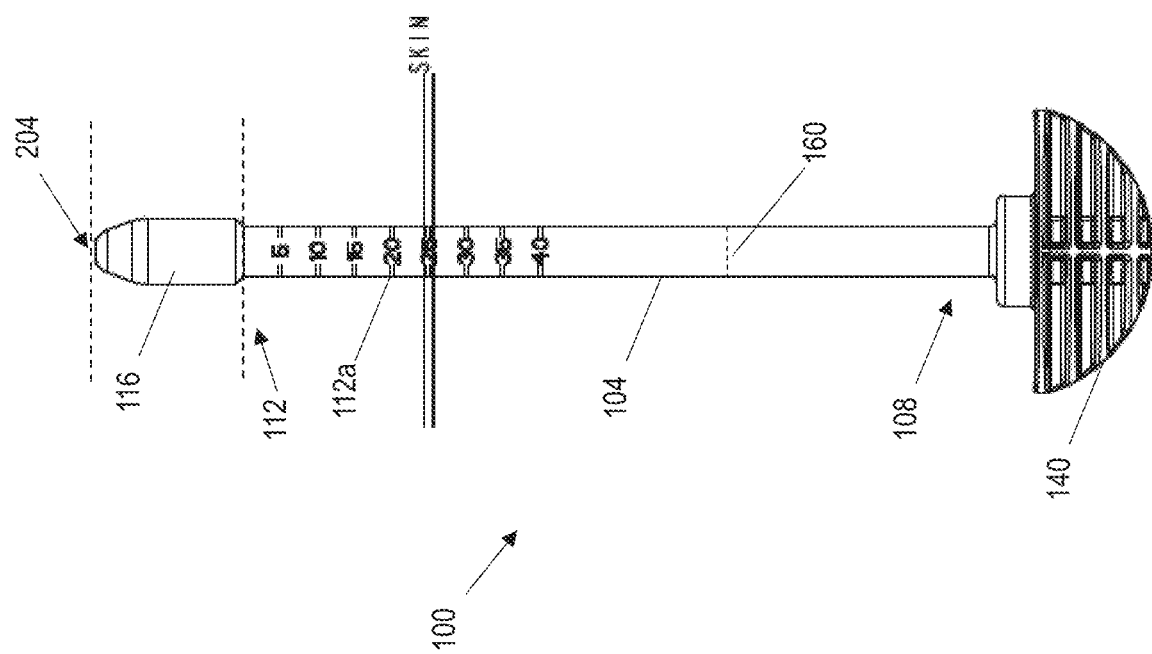
FIG. 1D shows a side view of the trial sizer of FIGS. 1A-1C inserted into an incision in skin to an insertion point located 25 mm below the skin surface.
Figure 1E:
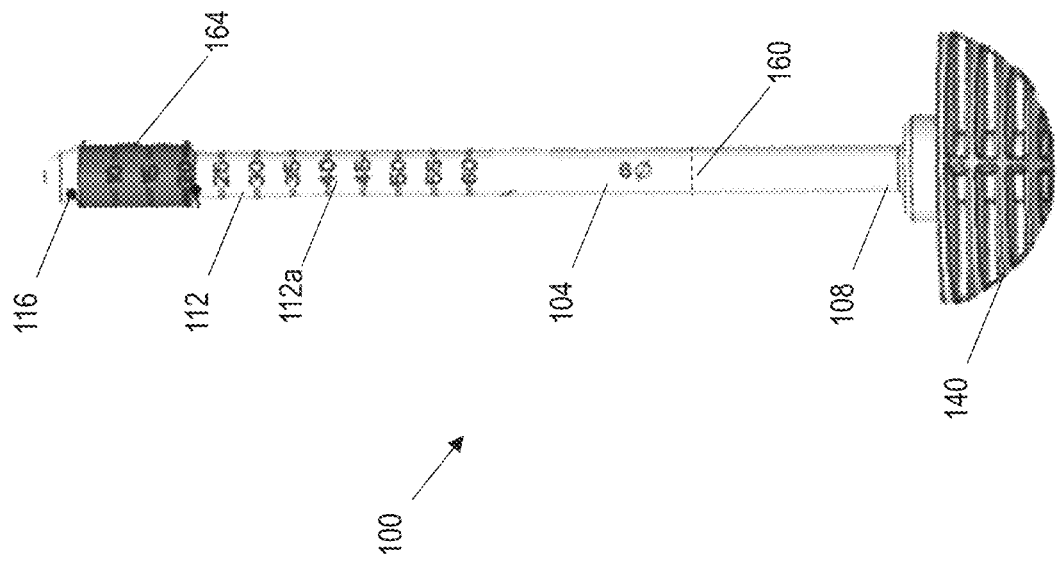
FIG. 1E shows a side view of a trial sizer with an extended depth range.

Referring to FIG. 1B, a cross-sectional view of trial sizer 100 is shown. In some configurations elongated shaft 104 defines a channel 128 extending from proximal end 108 to distal end 112. In some configurations, elongated shaft 104 is configured to indicate insertion depth of trial sizer 100 to correspond with the insertion depth of a soft-tissue allograft. For example, as shown in FIG. 1A, distal end 112 of elongated shaft 104 comprises a plurality of indicia 112a to indicate insertion depth of trial sizer 100 into a space (e.g., cavity such as sinus tarsi). For example, as best illustrated in FIGS. 1A and 1C, the indicia can be in the form of a depth scale. For example in some configurations, the depth scale may represent a range of dimensions (e.g., 5 mm to 40 mm) such that when trial sizer 100 is inserted into skin, as illustrated in FIG. 1D, depth scale will indicate the depth of insertion (e.g., 25 mm in FIG. 1D). In other configurations, depth scale may have a range with a low value is less than 5 mm and a high value that is greater than 40 mm. In some configurations the plurality of indicia 112a can have a depth scale that is greater than 40 mm. For example, as best illustrated in FIG. 1E, the plurality of indicia 112a may range from 10 mm to 60 mm. In other configurations, the depth scale can be any range between 0 mm and a length of elongated shaft 104.

In some configurations, distal end 112 of elongated shaft 104 defines one or more threads 132 along a portion of a length 136 of distal end 112. In some configurations, such as the one shown in FIG. 1B, trial sizer 100 may further include trial sizer handle 140 defining a channel 144 extending between, and through, a proximal end 148 to a distal end 152, the trial sizer handle 140 being coupled to proximal end 108 of elongated shaft 104. In some configurations, trial sizer handle 140 is unitary with elongated shaft 104. In some configurations, channel 144 is in fluid communication with channel 128 to define a passage through trial sizer 100. In some configurations, channel 128 has a transverse dimension that is less than a transverse dimension of channel 144, while in other configurations the transverse dimension channel 128 may be greater than or equal to the transverse dimension of channel 144.

In some configurations, radiopaque tip 116 can be uncoupled from distal end 112 of elongated shaft 104 and the elongated shaft can be used to push an implant (e.g., dermal allograft 700) through delivery cannula 200 to an insertion point 204 beneath the skin surface. In some configurations, the length of radiopaque tip 116 is from 8 mm to 25 mm. Radiopaque tip may comprise any suitable material that can absorb X-rays and thus influence a radiological image. In this way, trail sizer 100 may be used during a fluoroscopy procedure so an operator may precisely determine the location of radiopaque tip 116 while the tip is inserted within a patient.

Referring now to FIGS. 2A-4, some configurations of the present kits 400 comprise: at least one of the configurations of the presently disclosed trial sizers, and a delivery cannula 200, such as the one shown in FIGS. 2A-2C, comprising: an elongated body 208 having a proximal end 212 and a distal end 216, and defining a longitudinal channel 220 extending between, and through, the proximal and distal ends 212, 216; and a handle portion 224 coupled to proximal end 212 of elongated body 208, the handle portion 224 defining a channel 228 that is aligned with and in fluid communication with longitudinal channel 220 of elongated body 208. In some configurations of the present kits, elongated body 208 of delivery cannula 200 comprises transparent material to allow depth readings of the scale (e.g., 112a) located on elongated shaft 104 of trial sizer 100 or elongated shaft 304 of delivery tool 300.

In some configurations of the present kits 400, kit 400 further comprises delivery tool 300, such as the one shown in FIGS. 3A-3C. In the depicted configuration, delivery tool 300 comprises an elongated shaft 304 having a proximal end 308 and a distal end 312 that is configured to indicate insertion depth. In some configurations of the present kits, distal end 312 of elongated shaft 304 comprises a plurality of indicia 312a to indicate insertion depth. In some configurations of the present kits, elongated shaft 304 of delivery tool 300 has a diameter 316 from 5 mm to 15 mm. In some configurations of the present kits, delivery tool 300 further comprises delivery tool head 320 coupled to proximal end 308 of elongated shaft 304. In some configurations of the present kits, delivery tool head 320 is unitary with elongated shaft 304.

In some configurations of the present kits, elongated shaft 104 of trial sizer 100 is configured to have an outer diameter 160 from 5 mm to 15 mm. In some configurations of the present kits, delivery cannula 200 is configured to have an inner diameter 232 from 5 mm to 15 mm. Any combination of trial sizer 100 and delivery cannula 200 may be chosen to permit trial sizer 100 to fit within inner diameter 232 of delivery cannula 200 when sizing a soft-tissue allograft (e.g., dermal allograft 700) for delivery to insertion point 204.

Figure 5B:
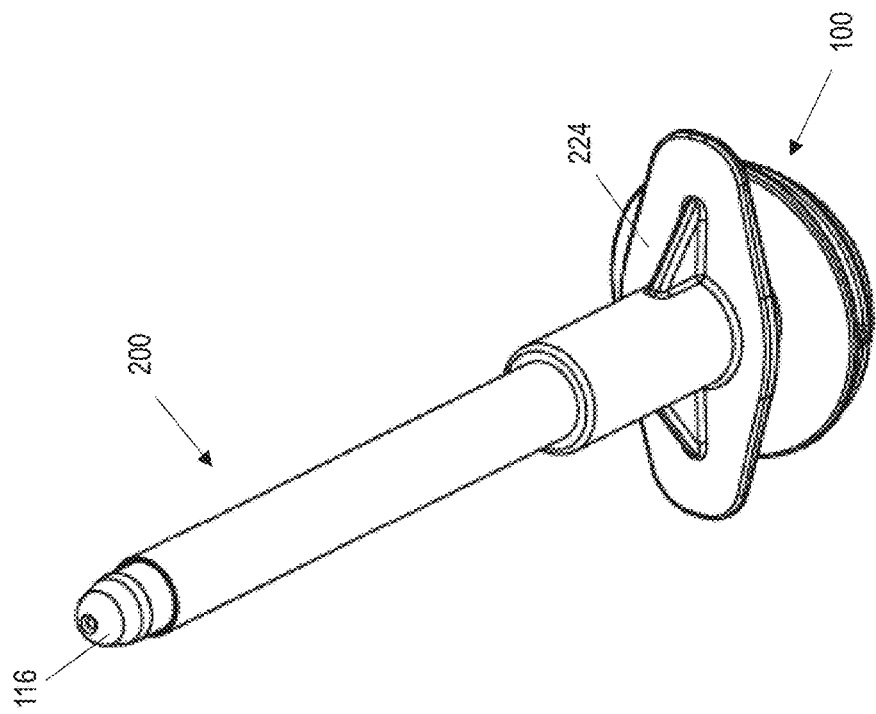
FIG. 5B shows an isometric view of the apparatus of FIG. 6A, with a portion of the tip of the trial sizer extending past the distal end of the delivery cannula.
Figure 5A:
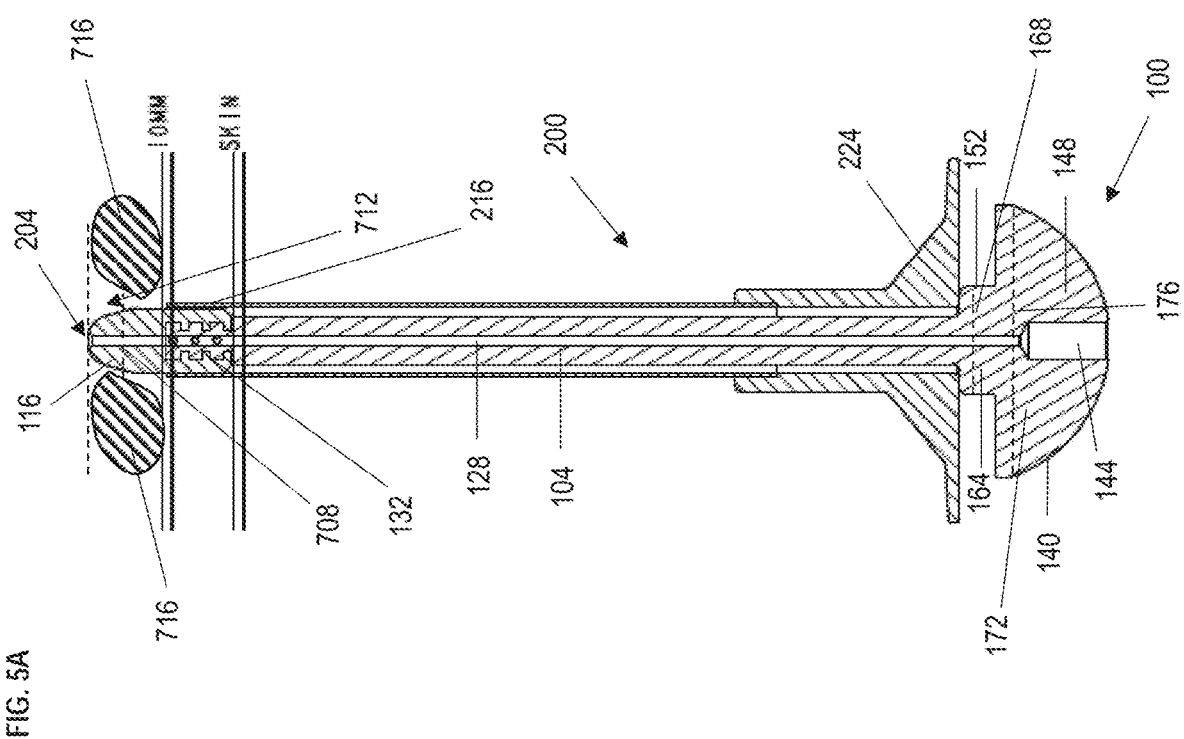
FIG. 5A shows a cross-sectional view of a configuration of the present trial sizers inserted into a configuration of the present delivery cannula, with the tip of the trial sizer extending past the distal end of the delivery cannula at least 10 mm beneath the skin surface.

As best illustrated by FIGS. 5A-5B, in some configurations of the present kits, distal end 152 of trial sizer handle 140 has a first portion 164 with a first transverse dimension 168, and a second portion 172 with a second transverse dimension 176 larger than first transverse dimension 168, the first transverse dimension 168 being larger than a corresponding transverse dimension 220a of longitudinal channel 220 of delivery cannula 200 to prevent the first portion 164 from entering longitudinal channel 220 of delivery cannula 200.

In some configurations of the present kits, kit 400 further comprises at least one sterile dermal allograft 700 having a diameter 704 about equal to an average width 708 of a canal 712 between a subject's misaligned bones 716, where dermal allograft 700 is compressible and flexible. In some configurations of the present kits, dermal allograft 700 has a density sufficient to resist full compression of canal 712.

In some configurations of the present kits, kit 400 further comprises a package 404 within which other components of kit 400 are sealed.

Referring to FIG. 6, a flow chart showing a method 600 for sizing and delivering a soft-tissue allograft using any of the configurations of the apparatuses and kits of the present disclosure is shown. The operation of method 600 will be described with reference to trial sizer 100, delivery cannula 200, and delivery tool 300, but may be performed with any of the configurations of the present trial sizers and kits of the present disclosure.

At block 604, and as illustrated by FIGS. 5A-5B, method 600 starts by disposing trial sizer 100 through an incision in the skin of a patient such that distal end 112 of trial sizer 100 is disposed between the incision and a given space between bones of the patient. The inserted trial sizer 100 may be operable with any of the presently disclosed kits or of the presently disclosed apparatuses. In some configurations, delivery cannula is disposed through the incision and trial sizer 100 is then inserted into the space. In some configurations, such as the one illustrated in FIGS. 5A-5B, delivery cannula 200 is inserted as deep into canal 712 as possible with the aid of trial sizer 100. At block 608, method 600 continues by determining whether trial sizer 100 fits into the space in an acceptable way, and if trial sizer 100 fits into the space in an acceptable way, continuing to block 612 by inserting a correspondingly sized delivery cannula 200 into the space (e.g., 712). If trial sizer 100 does not fit into the space in an acceptable way, method 600 continues to block 608a by sequentially repeating steps at blocks 608 and 608a with a trial sizer of a different size until a trial sizer fits into the space in an acceptable way.

Some methods comprise delivering an implant (e.g., dermal allograft implant 700) through cannula 200 into the space. To deliver the implant, some methods include removing trial sizer 100 from delivery cannula 200 and placing the implant (e.g., 700) into the cannula (e.g., inserting allograft implant into channel 228). The implant may then be pushed through delivery cannula 200 by reinserting trial sizer 100 or using a different tool (e.g., delivery tool 300). Some methods comprise disposing the implant into the space and removing trial sizer 100, delivery cannula 200, and/or delivery tool 300.

Delivery of a soft-tissue allograft (e.g., dermal allograft 700) may be performed using a trial sizer of any of the presently disclosed kits or of the presently disclosed apparatuses into the space including, for example, by uncoupling the radiopaque tip of the trial sizer and using the distal end of the elongated shaft of the trial sizer to push dermal allograft 700 through the delivery cannula to the insertion point. In some configurations, as illustrated by FIGS. 7A-7E, delivery of dermal allograft 700 into the space may be performed using trial sizer 100 of any of the presently disclosed kits or of the presently disclosed apparatuses. In other configurations, a delivery tool (e.g., 300) of any of the presently disclosed kits or of the presently disclosed apparatuses may be used to deliver an implant (e.g., 700) into the space including, for example, by using distal end 312 of elongated shaft 304 of delivery tool 300 to push dermal allograft 700 through delivery cannula 200 to the insertion point at a desired depth indicated on distal end 312 of delivery tool 300 visible through delivery cannula 200.

Referring to FIGS. 7F-7O, top and isometric views of a subtalar operation for inserting a dermal allograft 700 into a space 720 (e.g., sinus tarsi) within a patient's foot are shown. FIGS. 7F and 7G depict the trial sizer 100 inserted into space 720. A correctly dimension trial sizer 100 may be determining using the method disclosed in FIG. 6. FIGS. 7H and 7I show top and isometric views of trial sizer 100 and delivery cannula 200 inserted into space 720. In the depicted embodiment, delivery cannula 200 is inserted into space 720 before trial sizer 100; however, in other configurations, trial sizer 100 is inserted into the space before the delivery cannula.

Referring now to FIGS. 7L and 7M, top and isometric views of patient's foot are shown after trial sizer 100 is removed from space 720. As shown, a dermal allograft 700, or any other insert, may be placed within delivery cannula 200. The insert may then be delivered to space 720 via longitudinal channel 220 of delivery cannula 200. As shown in FIGS. 7N and 7O trial sizer 100 may be reinserted into delivery cannula 200 to deliver the insert into space 720. In other configurations, another tool may be used to deliver insert 700 through delivery cannula 200. For example, delivery tool 300 can be used to push the insert through longitudinal channel 220 of delivery cannula 200. Dermal allograft 700 is then disposed within space 720 (e.g., sinus tarsi) to help stabilize the skeletal or musculoskeletal system. For example, dermal allograft 700 is placed within the sinus tarsi to supplement the talocalcaneal ligament.

Some implementations of the present methods for sizing and delivering an allograft further comprise removing the delivery cannula after delivering the implant. In some configurations of the present methods for sizing and delivering an allograft, the method further comprises suturing the incision closed.

In some implementations of the present methods for sizing and delivering a soft-tissue allograft, delivery cannula 200 comprises an elongated body 208 having a proximal end 212 and a distal end 216, and defining a longitudinal channel 220 extending between, and through, proximal end 212 and distal end 216, and handle portion 224 coupled to proximal end 212 of elongated body 208, the handle portion 224 defining channel 228 that is aligned with and in fluid communication with longitudinal channel 220 of elongated body 208.

In some implementations of the present methods for sizing and delivering a soft-tissue allograft, the method further comprises inserting delivery tool 300 comprising an elongated shaft 304 having a proximal end 308 and a distal end 312, where distal end 312 of elongated shaft 304 is configured to indicate insertion depth.

Figure 8A:
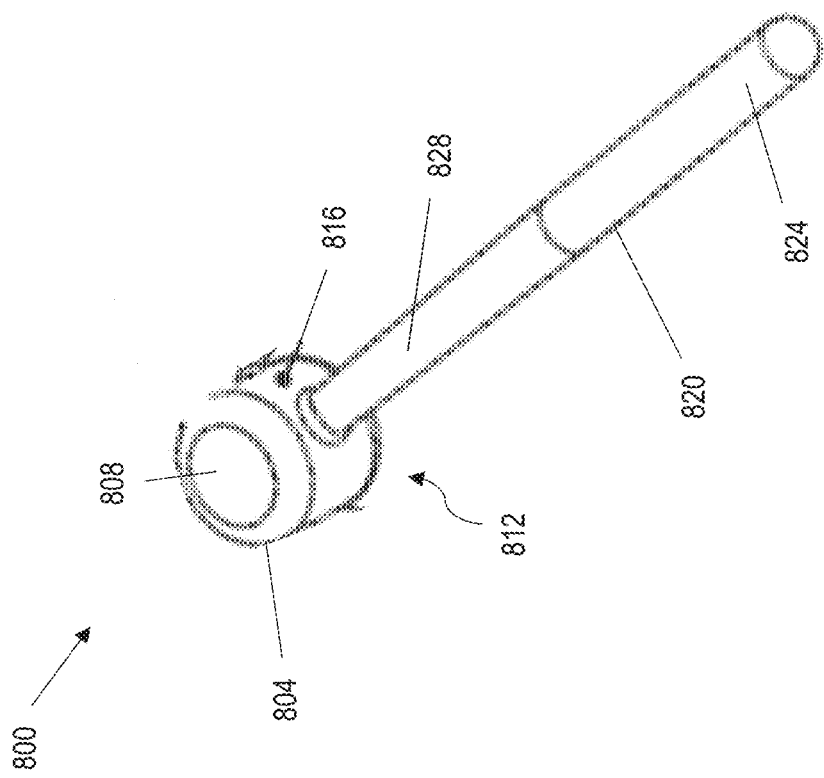
FIG. 8A shows an isometric view of another configuration of the present trial sizers.

FIG. 8A shows an isometric view of another configuration of the present trial sizers. In some configurations, trial sizer 800 includes a cylindrical head 804 with a first side 808, a second side 812, and a peripheral surface 816 extending between the first and second sides 808, 812, and may define, as shown, a circular cross sectional shape of the head 804, or any other shape particularly suited for the type of joint arthroplasty procedure. The handle 820 has a proximal end 824 and a distal end 828 coupled to the peripheral surface 816. The head 804 can have dimensions that mimic the dimensions of a corresponding soft-tissue allograft. In this way, at least some configurations of the present apparatuses can aid in determining the appropriate size and location of the soft-tissue allograft appropriate for transplantation at the site of delivery in a way that has previously not been possible with prior art trial sizers.

FIGS. 8B-8D show an isometric view, side view, and cross-sectional view of cylindrical head 804 of a present trial sizer. In some configurations, cylindrical head 804 may define one or more apertures (e.g., 832) going through peripheral surface 816. Aperture(s) 832 may be used to couple handle 820 to cylindrical head. Cylindrical head 804 can be sized and shaped to correspond to a soft-tissue allograft. For example, cylindrical head 804 has a length 834 that is be greater than or equal to any one of, or between any two of: 0.1, 0.2, 0.3, 0.4, 0.5, 0.6, or 0.75 inches (in.) (e.g., between 0.4 and 0.6 in, such as approximately 0.591 in.).

In some configurations, head 804 is radiopaque. In some configurations, the head 804 is unitary with the handle 820. In some configurations, a transverse dimension of the head 804 is from 8 mm to 20 mm.

Referring now to FIGS. 9A-9F, FIG. 9A shows a side view of a configuration of the present suture delivery guides. FIG. 9B shows a top view of the suture delivery guide of FIG. 9A. FIG. 9C shows a cross-sectional view of the suture passages disposed within the suture delivery guide of FIG. 9A and taken along a plane bisecting the suture delivery guide. FIG. 9D shows a cross-sectional side view of the suture delivery guide of FIG. 9A taken along a plane bisecting the longitudinal dimension of the suture delivery guide. FIG. 9E shows a cross-sectional top view of the suture delivery guide of FIG. 9D. FIG. 9F shows a cross-sectional view of the suture passages on a side of the implant chamber and taken along a plane bisecting the suture delivery guide. In some configurations, suture delivery guide 900 includes a body 904 having a first side 908 and a second side 912 and defining an implant chamber 916 extending through the first side 908 toward the second side 912, the body 904 defining a plurality of first suture passages 920 on a first side 924 of the implant chamber 916 and a plurality of second suture passages 928 on a second side 932 of the implant chamber 916, each of the second suture passages 928 being aligned with a corresponding one of the first suture passages 920, the body 904 further defining a first slot 936 extending through the first side 908 of the body 904 and in fluid communication with all of the first suture passages 920, and a second slot 940 extending through the first side 908 of the body 904 and in fluid communication with all of the second suture passages 928.

In some configurations, the body 904 has a medial portion 944 that defines the implant chamber 916 and two lateral portions 948a, 948b, on opposite sides of the medial portion 944. A first one of the lateral portions 948a defines the first suture passages 920, and a second one of the lateral portions 948b defines the second suture passages 928.

In some configurations, each of two of the first suture passages 920a and a corresponding each of two of the second suture passages 928a is intersected by a reference plane (B-B) that extends parallel to the first and second slots 936, 940, and through the first and second sides 908, 912, of the body 904.

In some configurations, a set of two of the first suture passages 920b and a corresponding set of two of the second suture passages 928b is arranged relative to a reference plane (B-B) that extends parallel to the first and second slots 936, 940, and through the first and second sides 908, 912, of the body 904, such that the set of two of the first suture passages 920b are disposed on opposite sides of the plane, and the corresponding set of two of the second suture passages 928b are disposed on opposite sides of the plane (B-B).

Figure 9I:
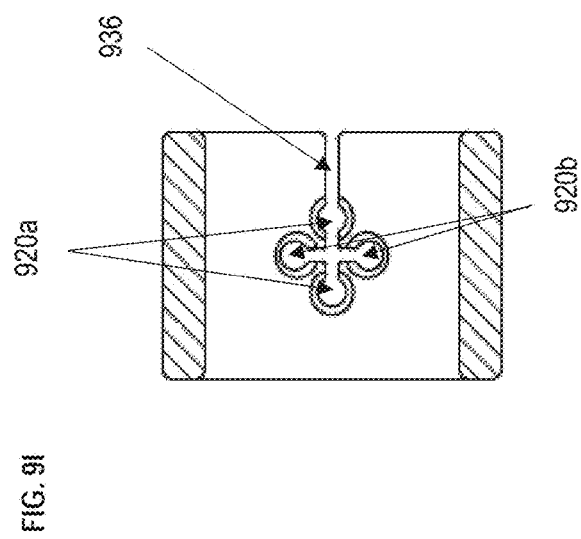
FIG. 9I shows a cross-sectional view of the suture passages on a side of the allograft chamber and taken along a plane bisecting the suture delivery guide of FIG. 9G.
Figure 9G:
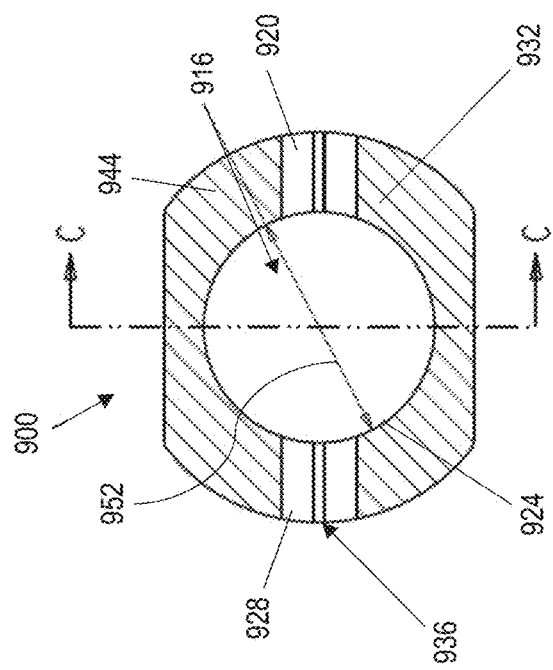
FIG. 9G shows a cross-sectional side view of a second configuration of the suture delivery guide taken along a plane bisecting the longitudinal dimension of the suture delivery guide.
Figure 9H:
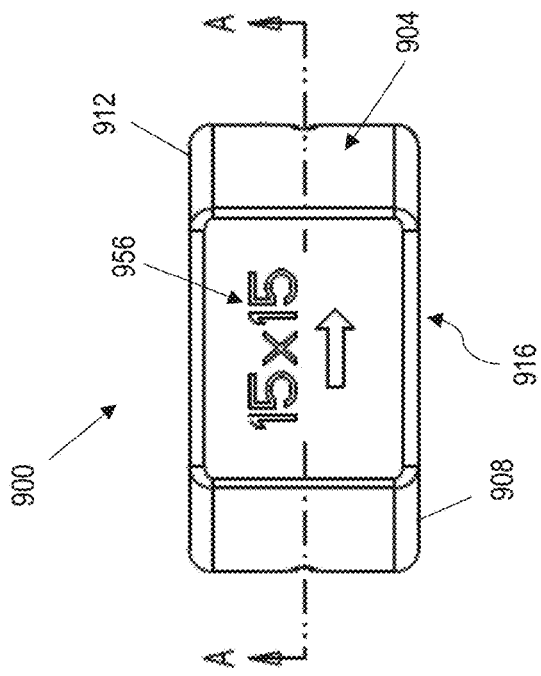
FIG. 9H shows a top view of the suture delivery guide of FIG. 9G.

Referring now to FIGS. 9G-9I, FIG. 9G shows a cross-sectional side view of a second configuration of the suture delivery guide. FIG. 9H shows a top view of the suture delivery guide of 9G. FIG. 9I shows a cross-sectional view of the suture passages on a side of the implant chamber and taken along a plane bisecting the suture delivery guide. In this configuration, components are similar (e.g., in structure and/or function) to components discussed with reference to FIGS. 9A-9F. In some configurations, implant chamber 916 comprises a maximum transverse dimension 952 between 4 mm to 20 mm. In some configurations, suture delivery guide 900 may contain a laser etching (e.g., 956) that contains information about the suture delivery guide. For example, a dimension, orientation, logo, or other information may be included in the laser etching.

In some configurations of the present kits, a kit comprises: at least one of a configuration of any of the presently disclosed trial sizers (e.g., 800); and at least one of a configuration of any of the presently disclosed suture delivery guides (e.g., 900).

In some configurations of the present kits, the kit further comprises: at least one sterile dermal allograft 516 having a diameter about equal to an average width of a canal between a subject's bones, where the dermal allograft 516 is compressible and flexible.

In some configurations of the present kits, the dermal allograft has a density sufficient to resist full compression.

In some configurations of the present kits, the kit further comprises a package within which the other components of the kit are sealed.

Implementation of the present methods will be discussed with reference to trial sizer 800, suture delivery guide 900 and the hand bones shown in FIGS. 11A-11C. FIG. 11A shows a top view of the thumb metacarpal bone 500, carpometacarpal joint 504, trapezium 508, and carpal bones 512 of the hand. FIG. 11B shows a sagittal view of the hand bones of FIG. 11A. FIG. 11C shows an isometric view of the hand bones of FIG. 11A.

In some implementations of the present methods, a method includes: (a) inserting a trial sizer (e.g., 800) of any of the kits presently disclosed or any configuration of the trial sizers presently disclosed into a given space between bones of the patient, such as, for example, the space occupied by the trapezium bone 508 in the carpometacarpal joint 504; (b) determining whether the trial sizer (e.g., 800) fits into the space in an acceptable way, and (i) if the trial sizer (e.g., 800) fits into the space in an acceptable way, delivering a soft-tissue allograft 516 to the space; or (ii) if the trial sizer (e.g., 800) does not fit into the space in an acceptable way, sequentially repeating steps (b) and (c) with a trial sizer of a different size until a trial sizer fits into the space in an acceptable way.

Figure 12B:
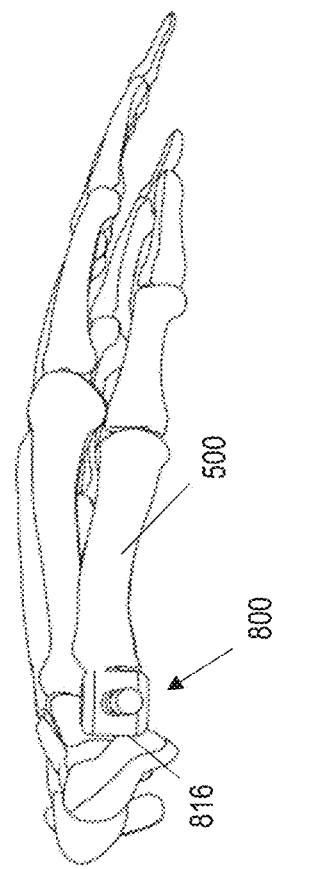
FIG. 12B shows a sagittal view of FIG. 12A.
Figure 12C:
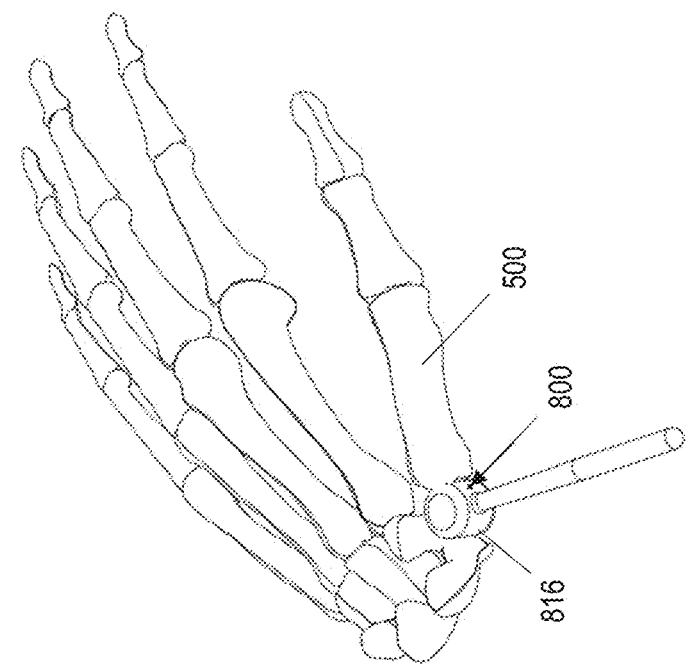
FIG. 12C shows an isometric view of FIG. 12A.
Figure 12A:
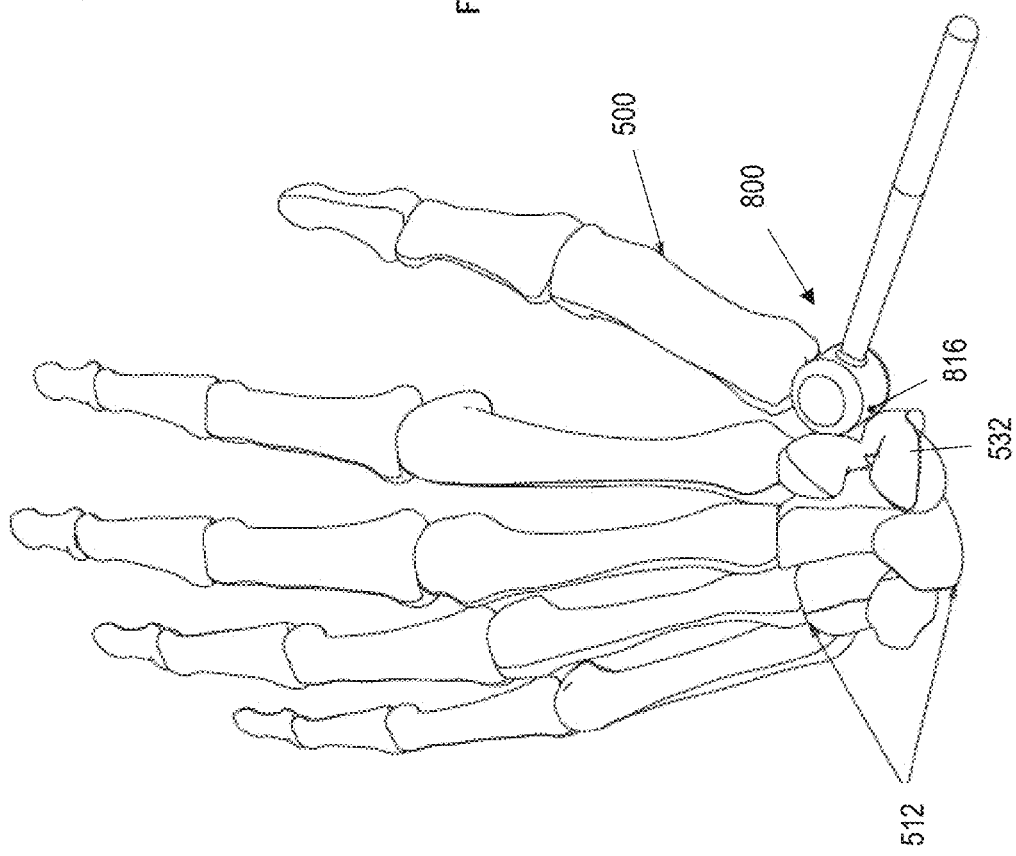
FIG. 12A shows a top view of the hand bones with the trial sizer of FIG. 8 oriented where the peripheral surface of the head of the trial sizer faces bone.
Figure 13B:
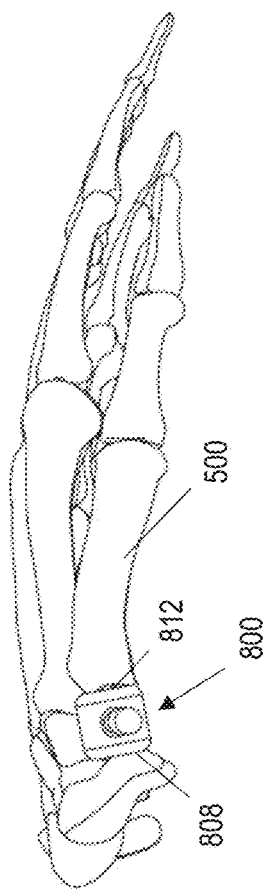
FIG. 13B shows a sagittal view of FIG. 13A.
Figure 13C:
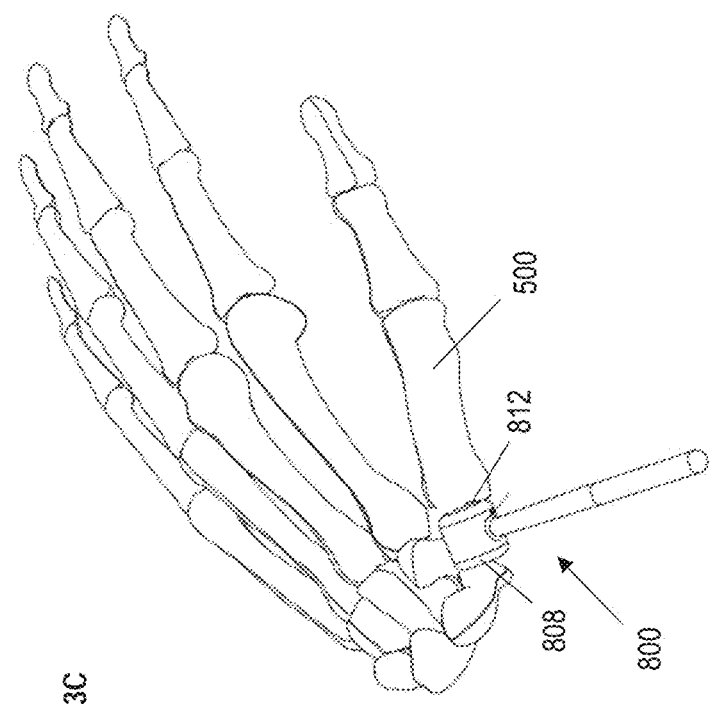
FIG. 13C shows an isometric view of FIG. 13A.
Figure 13A:
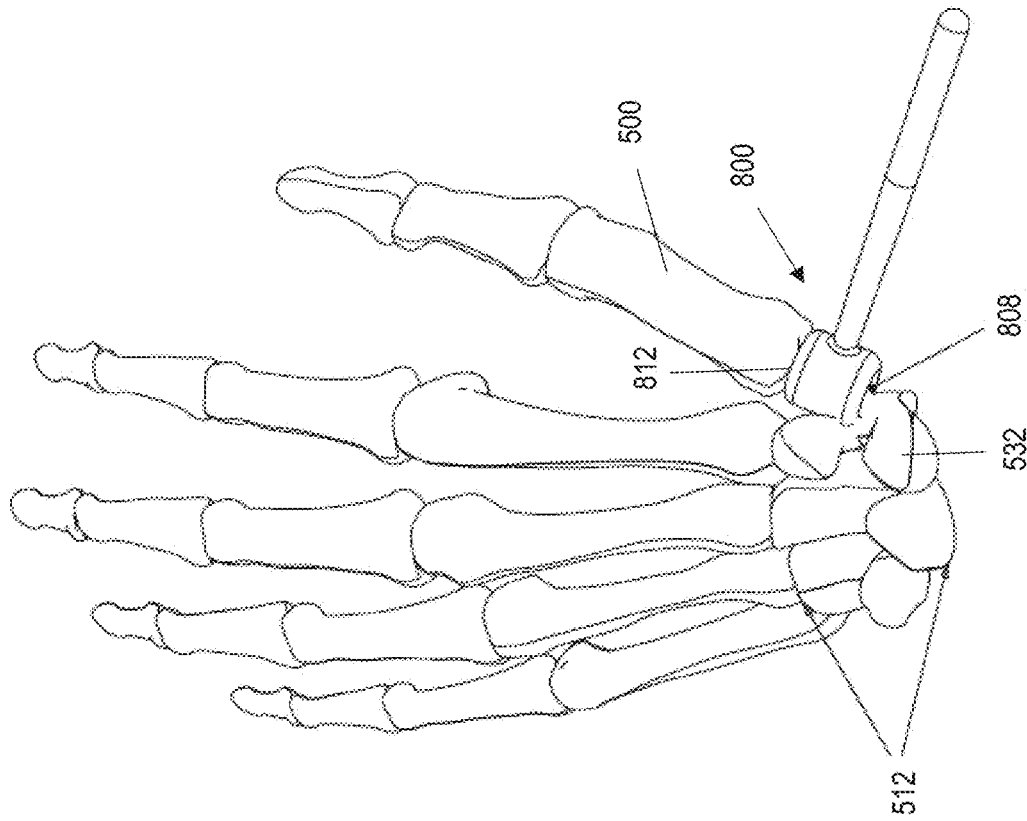
FIG. 13A shows a top view of the hand bones with the trial sizer of FIG. 8 oriented where the first and second sides of the head of the trial sizer face bone.

In some implementations, a bone (e.g., the trapezium bone 504) is excised prior to inserting trial sizer 800. As best illustrated in FIGS. 12A-12C, in some implementations the peripheral surface 816 of the head 804 of the trial sizer 800 faces bone in a preferred orientation. As best illustrated in FIGS. 13A-13C, in some implementations the first end 808 and the second end 812 of the head 804 of the trial sizer 800 faces bone in a preferred orientation.

Once the preferred orientation is determined, delivery of a soft-tissue allograft, such as dermal allograft 516, to the space between the bones may include using a suture delivery guide such as the one shown in FIGS. 9A-9F. The suture delivery guide may include any configuration of the suture delivery guides presently disclosed.

In some implementations, delivering an implant 516 to the space includes: inserting a suture anchor in the distal aspect of the 2nd metacarpal bone 520; and fastening a soft-tissue allograft 516 to the suture anchor.

Figure 10A:
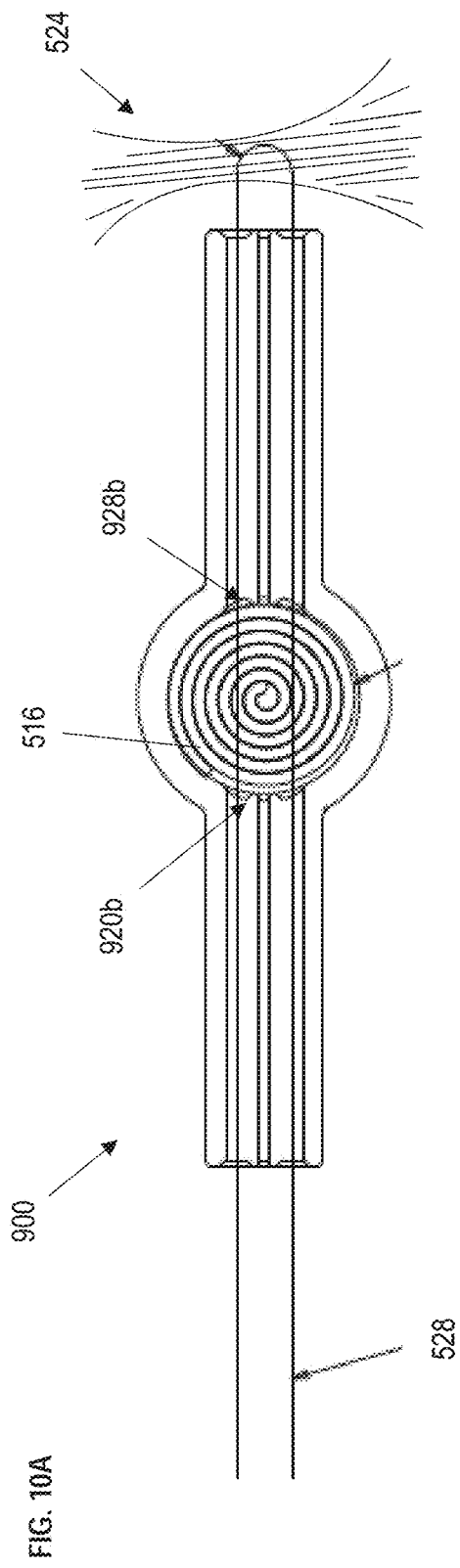
FIG. 10A shows a side view of the suture delivery guide of FIGS. 9A-9F with a suture looping through an allograft and back within the implant chamber.
Figure 10B:
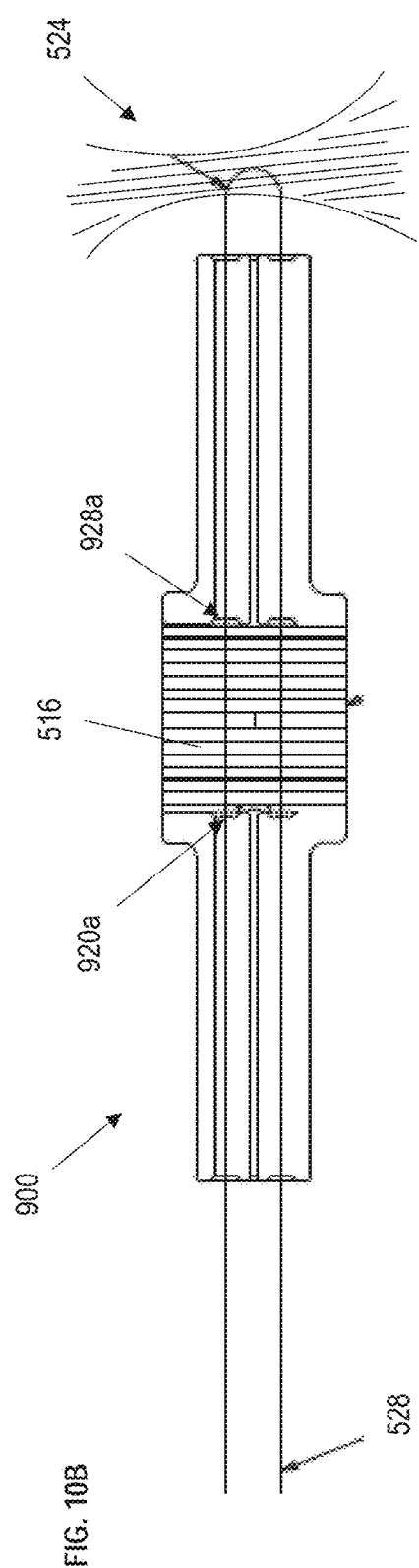
FIG. 10B shows a top view of the suture delivery guide of FIG. 10A.
Figure 15B:
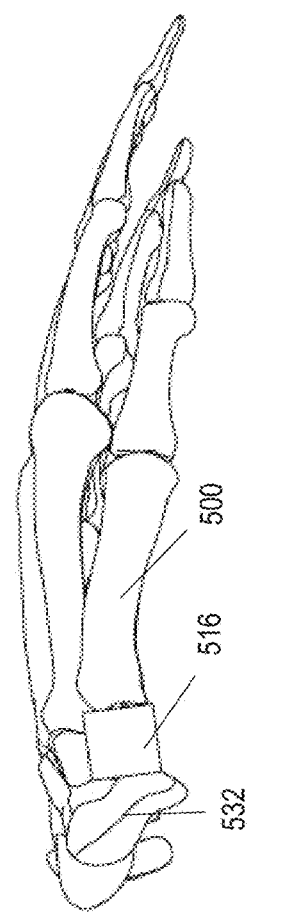
FIG. 15B shows a sagittal view of FIG. 15A.
Figure 15C:
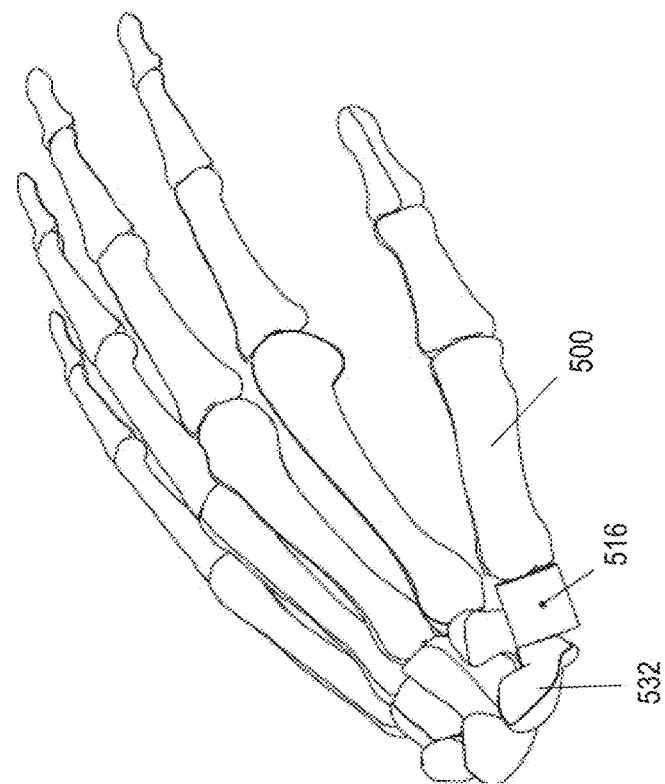
FIG. 15C shows an isometric view of FIG. 15A.
Figure 15A:
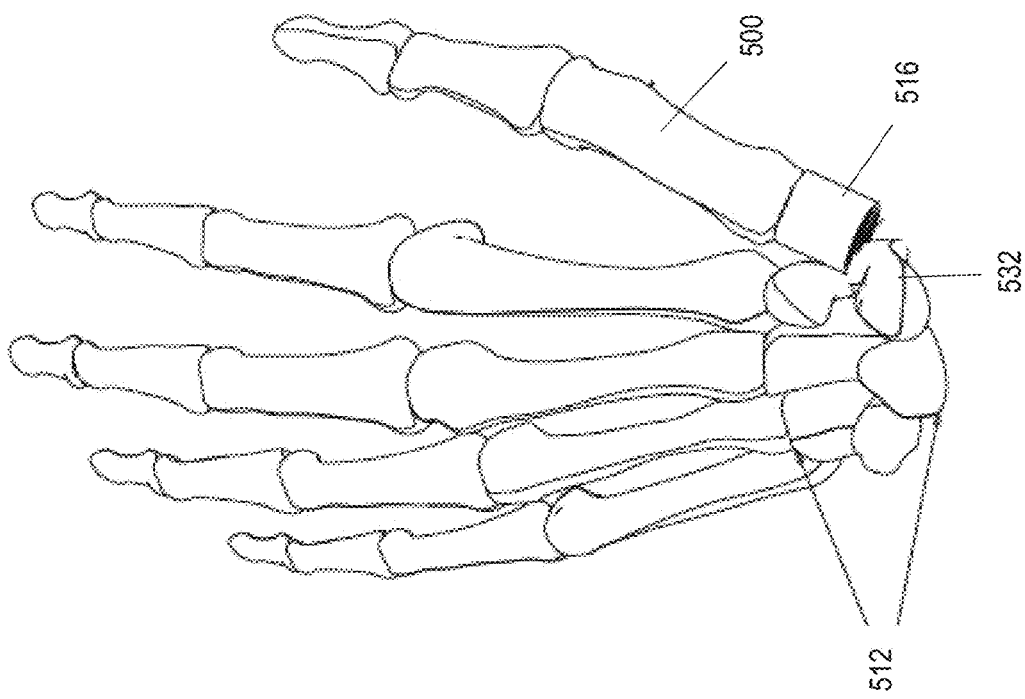
FIG. 15A shows a top view of the hand bones with an allograft disposed in a second orientation similar to the orientation of the trial sizer in FIG. 13A.

Referring now to FIGS. 9A-9F, and 10A-10B, delivery of a soft-tissue allograft 516 to the space in the same orientation as the trial sizer 800 of FIGS. 13A-13C using suture delivery guide 900 will be described. As best illustrated by FIG. 10B, in some implementations, delivering a soft-tissue allograft 516 to the space includes passing a suture 528 through one of a first set of suture passages 920a, through implant 516, and then through a corresponding one of a second set of suture passages 928a, and then looping the suture 528 through a flexor carpi radialis tendon 524 of the patient. The suture 528 is then looped back through the other one of the second set of suture passages 928a, back through soft-tissue allograft 516, and then through the other one of the first set of suture passages 920a. The suture 528 is then slipped out of first and second slots 936, 940, allowing the dermal allograft 516 to be delivered over the suture 528 and into the space between bones of the patient (e.g., as shown in FIGS. 15A-15C, the space previously occupied by the trapezium bone between the 1$^{st}$ metacarpal bone 500 and the scaphoid bone 532); and (d) tying the suture 528 using an acceptable surgical knot.

Alternatively, in some implementations, delivering an implant 516 to the space can be in the same orientation as the trial sizer 800 of FIGS. 12A-12C. As best illustrated by FIG. 10A, in some implementations, delivering a soft-tissue allograft 516 to the space includes passing a suture 528 through one of a first set of suture passages 920b, through implant 516, and then through a corresponding one of a second set of suture passages 928b, and then looping the suture 528 through a flexor carpi radialis tendon 524 of the patient. The suture 528 is then looped back through the other one of the second set of suture passages 928b, back through implant 516, and then through the other one of the first set of suture passages 920b. The suture 528 is then slipped out of first and second slots 936, 940, allowing the dermal allograft 516 to be delivered over the suture 528 and into the space between bones of the patient (e.g., as shown in FIGS. 14A-14C, the space previously occupied by the trapezium bone between the 1$^{st}$ metacarpal bone 500 and the scaphoid bone 532); and (d) tying the suture 528 using an acceptable surgical knot.

In some implementations of the present methods, a method comprises: providing at least one sterile pre-formed allograft rod plug having a diameter about equal to an average width of a space between a person's bones and a density sufficient to resist full compression of the space, the pre-formed allograft rod plug being resiliently compressible and flexible while remaining substantially as the formed plug; and delivering the at least one sterile pre-formed allograft rod plug into the space between a set of bones of the patient, where the set of bones is selected from the group of sets of bones consisting of: (a) a 1$^{st}$ metacarpal bone and a scaphoid bone; (b) a 4$^{th}$ metatarsal, 5$^{th}$ metatarsal bone, and cuboid bone; (c) a 5$^{th}$ metatarsal bone; (d) a tibia bone and a talus bone; (e) a radius bone and a humerus bone; (f) a femur bone and a pelvis bone; (g) any of the proximal phalanges of a hand and any of the corresponding intermediate phalanges of a hand.

In some implementations, a portion or all of a patient's trapezium bone is removed to manually create a space prior to delivering the at least one sterile dermal allograft.

In some implementations, a trial sizer (e.g., 800) is inserted into the space created between the 1$^{st}$ metacarpal 500 and the scaphoid bone 532 of the patient's hand prior to delivering the at least one sterile dermal allograft 516. For example, as shown in FIGS. 12A-12C, trial sizer 800 may be oriented where the peripheral surface 816 of the head 804 of the trial sizer 800 faces bone, or alternatively oriented where the first and second sides 808, 812, of the head 804 of trial sizer 800 face bone. Whichever orientation is determined by the health care provider to be an acceptable orientation, the dermal allograft 516 may then be delivered and oriented similarly. For example, as shown in FIGS. 14A-14C, dermal allograft 516 is oriented in a first orientation similar to the orientation of the trial sizer in FIGS. 12A-12C. Alternatively, as shown in FIGS. 15A-15C, dermal allograft 516 is oriented in a second orientation similar to the orientation of the trial sizer in FIGS. 13A-13C.

In some implementations, the space to be filled with dermal allograft 516 is between the 4$^{th}$ and 5$^{th}$ metatarsal bones of the foot and the cuboid bone of the foot.

In some implementations, the space to be filled with dermal allograft 516 is between a tibia bone and a talus bone of the patient.

In some implementations, the space to be filled with dermal allograft 516 is between a radius bone and a capitellum portion of a humerus bone of the patient.

In some implementations, the space to be filled with dermal allograft 516 is between a femur bone and a pelvis bone of the patient.

In some implementations, the space to be filled with dermal allograft 516 is between any of the proximal phalanges of a hand and any of the corresponding intermediate phalanges of a hand. Other clinical indications may also benefit from implementation of the methods presently disclosed.

The above specification and examples provide a complete description of the structure and use of exemplary configurations. Although certain configurations have been described above with a certain degree of particularity, or with reference to one or more individual configurations, those skilled in the art could make numerous alterations to the disclosed configurations without departing from the scope of this invention. As such, the various illustrative configurations of the present devices, apparatuses, kits, and methods are not intended to be limited to the particular forms disclosed. Rather, they include all modifications and alternatives falling within the scope of the claims, and configurations other than the one shown may include some or all of the features of the depicted configuration. For example, components may be combined as a unitary structure, and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one configuration or may relate to several configurations.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. An apparatus for delivering an insert into a space between a patient's bones, the apparatus comprising: a trial sizer, comprising: an elongated shaft having a proximal end and a distal end; a radiopaque tip coupled to the distal end of the elongated shaft, the radiopaque tip having a transverse dimension greater than a corresponding transverse dimension of the elongated shaft, and the radiopaque tip having dimensions that mimic the dimensions of a corresponding soft-tissue allograft, and further comprising a trial sizer handle coupled to the proximal end of the elongated shaft, the trial sizer handle having a proximal handle end and a distal handle end, where a diameter of the trial sizer handle at the distal handle end is greater than a diameter of the trial sizer handle at the proximal handle end, where the trial sizer handle defines a channel extending between, and through, the proximal handle end to the distal handle end.

2. The apparatus of claim 1, where the elongated shaft of the trial sizer defines a channel extending from the proximal end to the distal end, and where the elongated shaft is configured to indicate insertion depth.

3. The apparatus of claim 1, where the radiopaque tip is detachable from the distal end of the elongated shaft.

4. The apparatus of claim 1, further comprising:
a delivery cannula comprising:
an elongated body having a proximal end and a distal end, and defining a longitudinal channel extending between and through the proximal and distal ends; and
a handle portion coupled to the proximal end of the elongated body, the handle portion defining a channel that is aligned with and in fluid communication with the longitudinal channel of the elongated body.

5. The apparatus of claim 4, where the elongated body of the delivery cannula comprises transparent material.

6. The apparatus of claim 4, where:
the elongated shaft of the trial sizer comprises an outer diameter from 5 mm to 15 mm;
the delivery cannula comprises an inner diameter from 5 mm to 15 mm; and
the outer diameter of the elongated shaft is less than or equal to the inner diameter of the delivery cannula.

7. The apparatus of claim 1, where:
the radiopaque tip comprises a cylindrical head having a first side, a second side, and a peripheral surface extending between the first side and the second side and defining a circular cross sectional shape of the cylindrical head; and where the trial sizer further comprises a handle having a proximal end and a distal end coupled to the peripheral surface.

8. The apparatus of claim 7, where a transverse dimension of the cylindrical head is from 8 millimeters (mm) to 20 mm.

9. The apparatus of claim 1, where, for multiple points between the proximal handle end and the distal handle end on an axis through the trial sizer handle, a diameter of the trial sizer handle at each of the multiple points is greater than the diameter of the trial sizer handle at the proximal handle end and less than the diameter of the trial sizer handle at the distal handle end.

10. The apparatus of claim 1, where the trial sizer handle is unitary with the elongated shaft.

11. The apparatus of claim 1, where the radiopaque tip comprises a material that absorbs X-rays.

\* \* \* \* \*